United States Patent [19]
Bonutti

[11] Patent Number: 5,577,503
[45] Date of Patent: Nov. 26, 1996

[54] APPARATUS AND METHOD FOR USE IN MEDICAL IMAGING

[75] Inventor: Peter M. Bonutti, Effingham, Ill.

[73] Assignee: Apogee Medical Products, Inc., Effingham, Ill.

[21] Appl. No.: 221,848

[22] Filed: Apr. 1, 1994

Related U.S. Application Data

[62] Division of Ser. No. 802,358, Dec. 4, 1991, Pat. No. 5,349,956.

[51] Int. Cl.$^6$ .................................................. A61B 5/055
[52] U.S. Cl. .................................. 128/653.2; 128/653.5; 5/612; 5/622; 5/624
[58] Field of Search ............................. 128/653.1, 653.2, 128/653.5, 781, 782, 774; 5/601, 612, 621–624; 324/309, 318

[56] References Cited

U.S. PATENT DOCUMENTS

| | | |
|---|---|---|
| 1,239,146 | 9/1917 | Wantz . |
| 2,801,142 | 7/1957 | Adams . |
| 2,972,505 | 2/1961 | Weickgenannt . |
| 3,025,397 | 3/1962 | Travis et al. . |
| 3,124,328 | 3/1964 | Kortsch . |
| 3,521,876 | 7/1970 | Smith . |
| 3,528,413 | 9/1970 | Aydt . |
| 3,766,384 | 10/1973 | Anderson . |
| 4,050,355 | 9/1977 | Niskanen . |
| 4,232,681 | 11/1980 | Tulaszewski . |
| 4,256,112 | 3/1981 | Kopf et al. . |
| 4,291,229 | 9/1981 | Patt . |
| 4,323,080 | 4/1982 | Melhart . |
| 4,407,277 | 10/1983 | Ellison . |
| 4,562,588 | 12/1985 | Ruf . |
| 4,616,814 | 10/1986 | Harwood-Nash et al. . |
| 4,681,308 | 7/1987 | Rice . |
| 4,717,133 | 1/1988 | Walsh et al. . |
| 4,791,372 | 12/1988 | Kirk et al. ............................... 324/318 |
| 4,827,496 | 5/1989 | Cheney . |
| 5,001,739 | 3/1991 | Fischer . |
| 5,007,912 | 4/1991 | Albrektsson et al. . |
| 5,078,140 | 1/1992 | Kwoh . |
| 5,154,178 | 10/1992 | Shah ...................................... 128/653.5 |
| 5,305,750 | 4/1994 | Makita ................................. 128/653.5 |

OTHER PUBLICATIONS

"Patellofemoral Joint Abnormalities in Athletes: Evaluation by Kinematic Magnetic Resonance Imaging" by Frank G. Shellock, PhD. published in vol. 3; Issue 4; 1991 of Topics in Magnetic Resonance Imaging, pp. 71–95.

*Primary Examiner*—Ruth S. Smith
*Attorney, Agent, or Firm*—Tarolli, Sundheim, Covell, Tummino & Szabo

[57] ABSTRACT

An apparatus and method for use in medical imaging simulate within an imaging coil normal movements of body parts such as joints, and improve imaging of soft tissue and bony parts as compared to a static system in which images are taken of a joint in only one position. A joint or body parts is moved into various positions in multiple planes within its range of motion while a series of images are taken of the joint in the different positions. The images are collated into a cine format to effectively show the joint in motion. A surface or volume coil may be coupled for movement with the joint or body part and maintained in the proper spatial relationship with the primary coil's electromagnetic field. The systems may be provided as mechanisms usable with existing imaging tables to reduce cost, or may be built into a new imaging table. It is possible to use a larger primary coil, allowing increased range of movement. Traction may be applied to a joint being imaged, in order to load the joint.

76 Claims, 16 Drawing Sheets

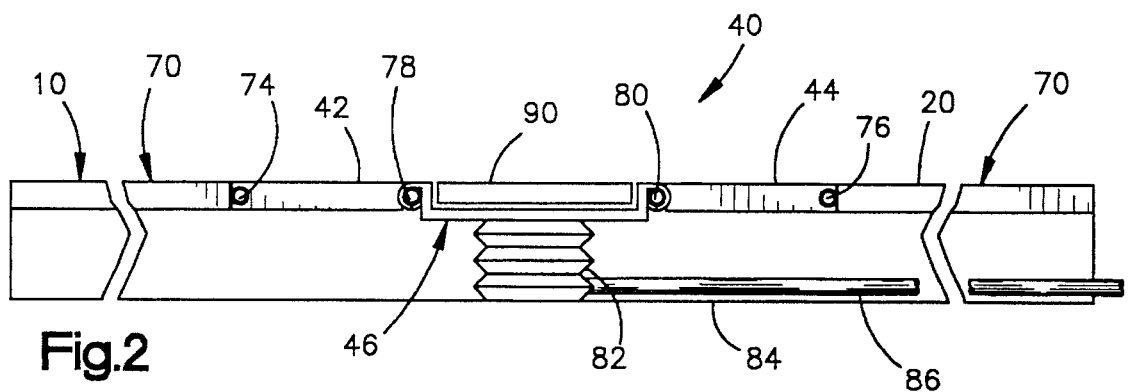
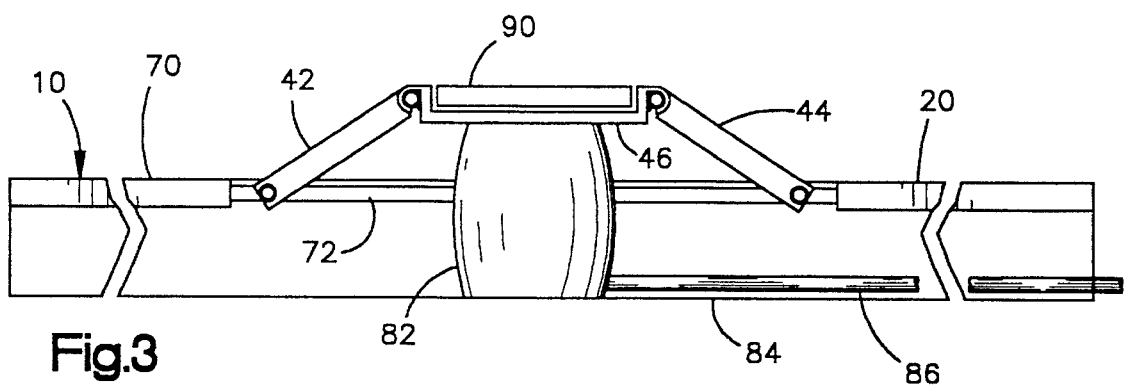
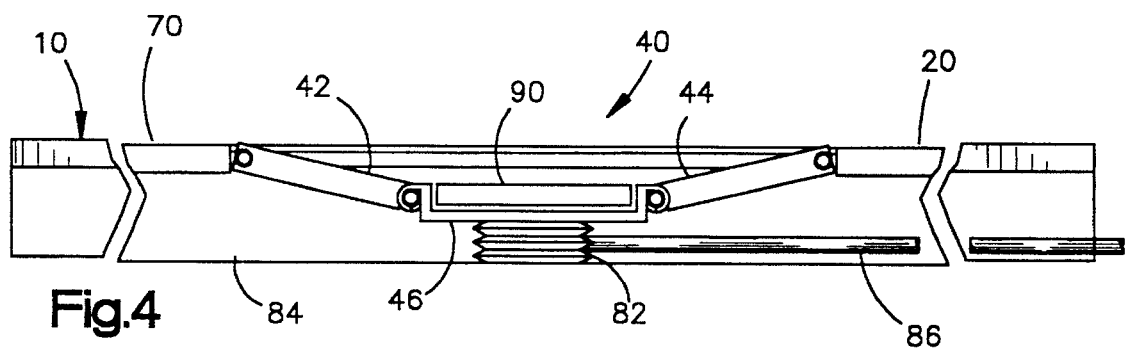
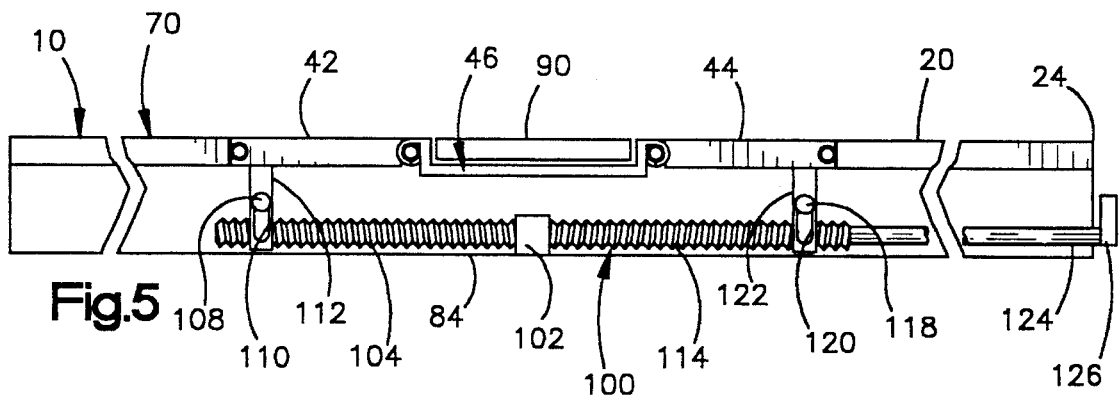

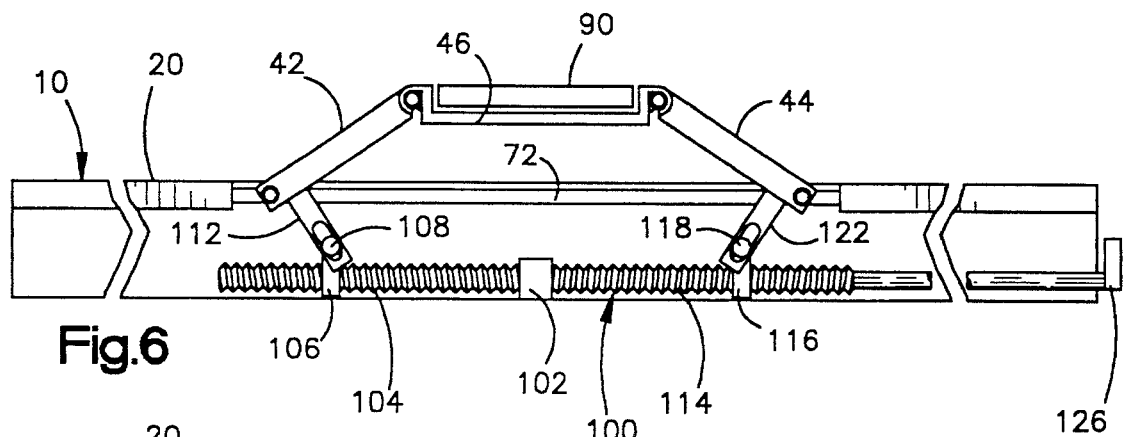
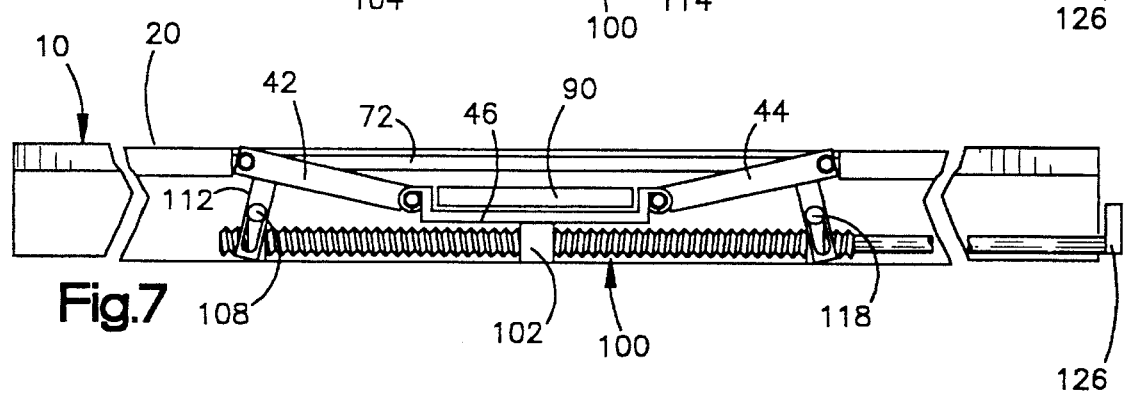
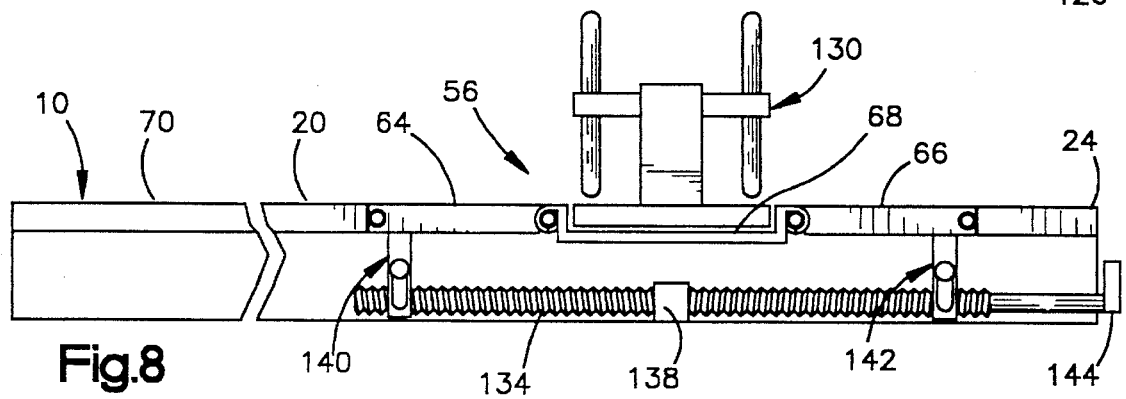
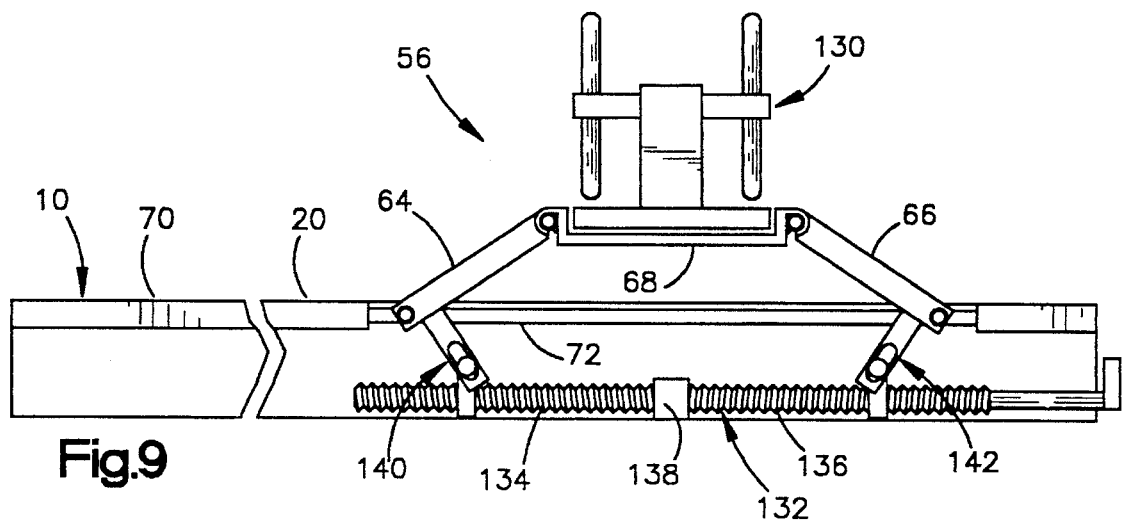

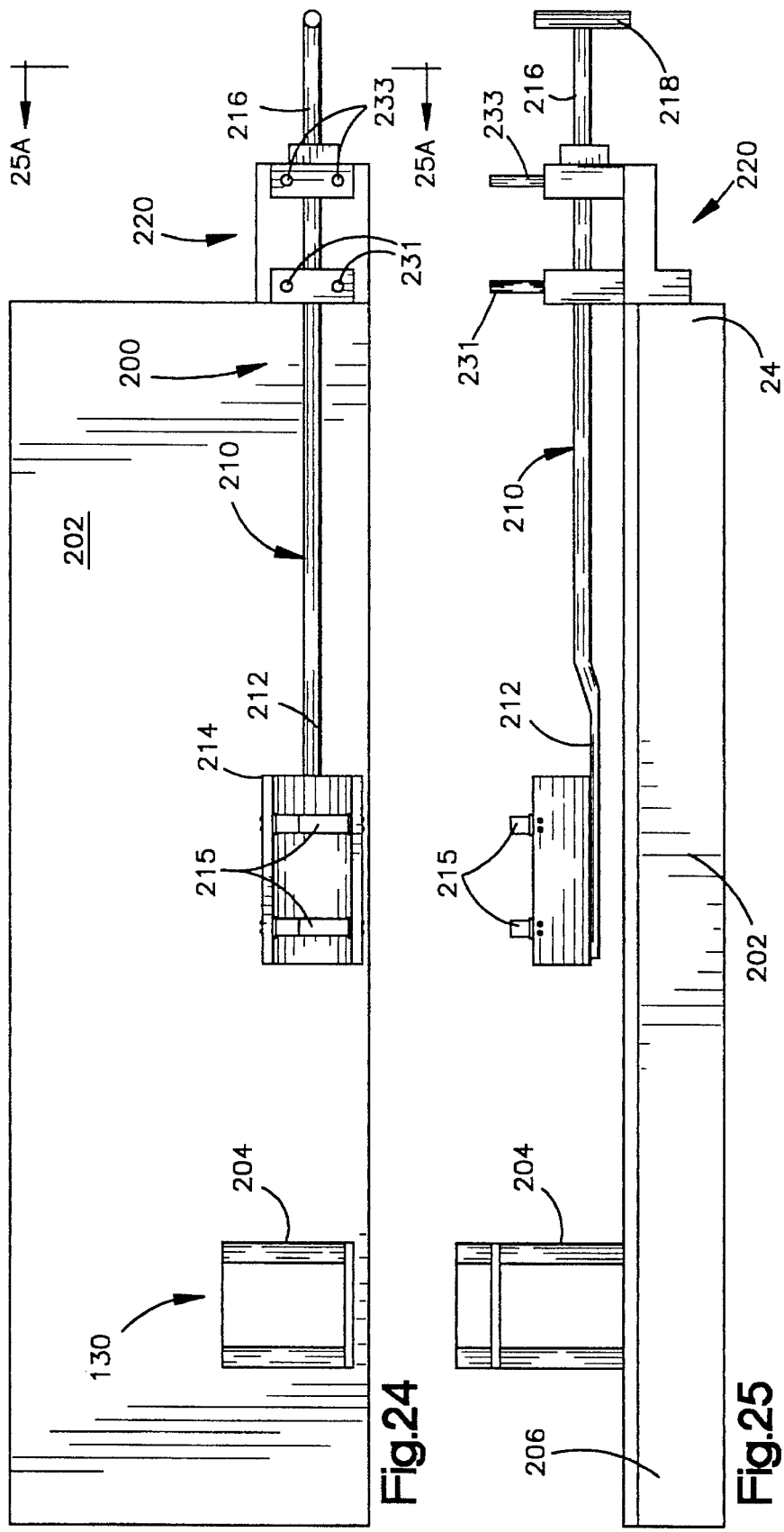

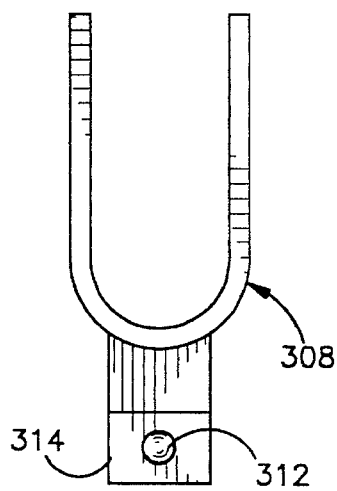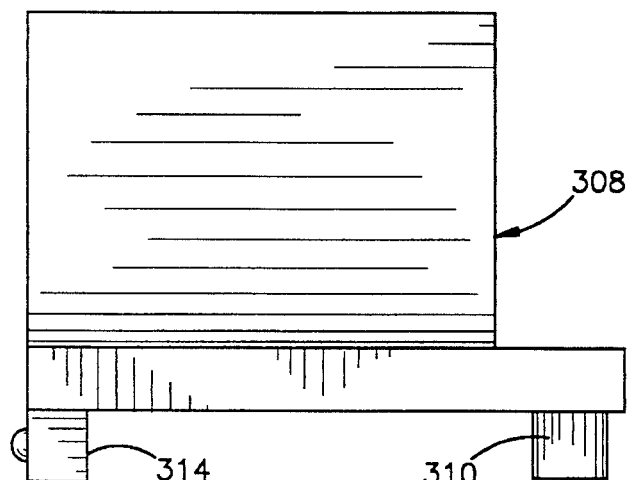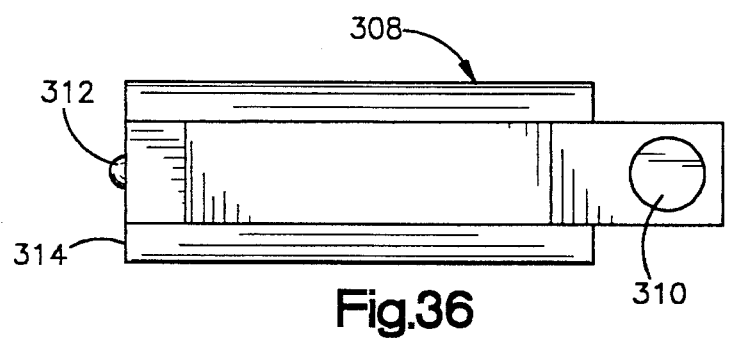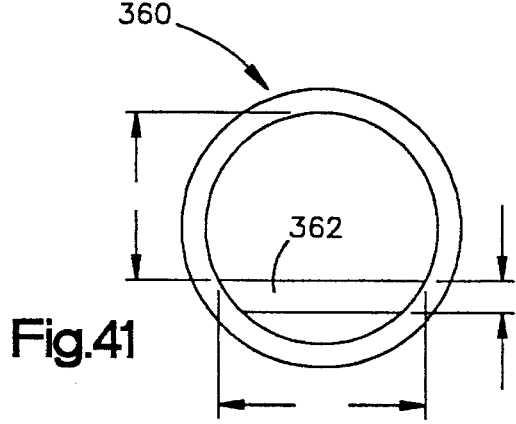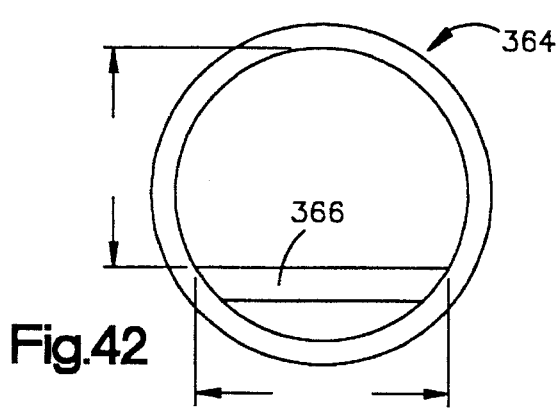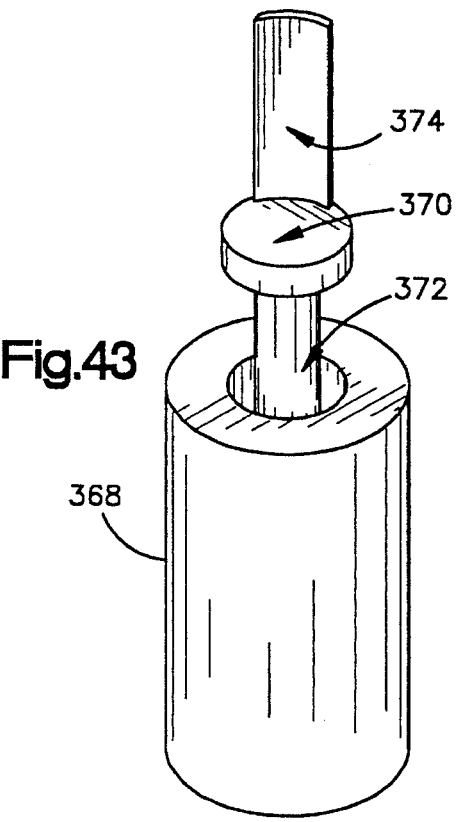
Fig.34
Fig.35
Fig.36
Fig.41
Fig.42
Fig.43

5,577,503

APPARATUS AND METHOD FOR USE IN MEDICAL IMAGING

This application is a divisional of application Ser. No. 07/802,358 filed on Dec. 4, 1991 which has issued as U.S. Pat. No. 5,349,956.

BACKGROUND OF THE INVENTION

The present invention relates to an apparatus and method for use in medical imaging. More particularly, the present invention relates to apparatus and method for positioning a patient and/or a secondary imaging coil inside a primary imaging coil.

In magnetic resonance imaging, a patient is placed inside a coil (the "primary" coil) which is large enough in diameter to receive the patient while he is lying prone on a table slidable into and out of the coil. A selected portion of the patient is then imaged by the use of electromagnetic radiation from the primary coil.

It is known to place smaller coils, called surface or volume coils, in close proximity to the specific part of the patient to be imaged, such as the neck, spine, or knee. These coils, referred to herein as secondary coils, are used to increase resolution by having a coil closer to the part to be imaged. It is essential to place the secondary coil in a particular orientation relative to the electromagnetic field generated by the primary coil.

Current imaging systems can only take images while a patient is in one particular position. One known device allows the patient to move his knee joint to different selected positions while the patient is in the primary coil. This device requires the patient to lie face down in the primary coil, which is extremely uncomfortable for the extended period of time required to image properly, especially in the close, almost claustrophobic confines of a primary MRI coil.

SUMMARY OF THE INVENTION

The present invention is an apparatus and method for use in medical imaging. The present invention provides a system to simulate within an imaging coil normal movements of body parts such as joints, and to improve imaging of soft tissue and bony parts as compared to a static system in which images are taken of a joint in only one position.

In accordance with a first aspect of the present invention, there is provided controlled motion of an extremity, while in an imaging coil, either patient directed or operator directed. A joint or body part is moved into various positions in multiple planes within its range of motion while a series of images are taken of the joint in the different positions. These individual images may then be collated into a cine format to effectively show the joint in motion. Thus, the present invention allows for studying a joint in motion and also allows for studying a joint or other body part at any positions within its range of motion allowable within the confines of the primary coil.

In accordance with a second aspect of the present invention, a surface or volume coil (referred to herein as a secondary coil) is coupled for movement with the joint or body part. The secondary coil is maintained in the proper spatial relationship with the primary coil's electromagnetic field. Keeping the secondary coil as close as possible to the joint or tissue being imaged, while moving the joint or body part, provides greatly enhanced resolution and more detail in the final image.

Thus, to illustrate these first two aspects of the invention in knee imaging, the knee is fixed by holding the upper and lower legs with cuffs and a secondary coil is placed around the knee itself. The knee is then imaged at 0° by using the primary and secondary coils. The knee is then flexed (either by the patient or the operator), and the secondary coil moves with the knee. The knee is progressively moved through various positions within its range of motion as limited only by the size of the primary coil. Images are taken at each position. The images may then be collated and shown in sequence to visualize the movement of the knee joint, or may be studied individually to study the joint at each position.

Similar systems are available for other joints, the back, neck, etc. These systems all are preferably provided as mechanisms usable with existing imaging tables to reduce cost. Alternatively, some of these may be built into a new imaging table.

Coupling a surface coil for movement with the extremity provides the necessary detail in the images, even with a larger primary coil, which is not available with present systems. Accordingly, it is possible to use a. larger diameter primary coil, allowing this increased range of movement, without the degradation in image quality which would be expected from the increased coil size. For example, the knee could be flexed through its entire range of motion to allow optimum imaging of the knee joint. This is currently impossible with the known small primary coils which only allow about 50° of flexion.

In accordance with another aspect of the present invention, traction is applied to a joint being imaged, in order to load the joint. This can simulate normal loading of a joint. Distracting a joint can also allow a better view of the parts of the joint and thus an increased imaging benefit. It can also allow simulation of normal loading of a joint, such as when carrying a heavy object or performing an athletic or work-related task. This feature is not available with present imaging apparatus. Traction can also be applied to a joint being imaged when the joint is in various positions, to simulate normal loading of a joint within its range of motion. Again, this feature is not available with present imaging apparatus.

BRIEF DESCRIPTION OF THE DRAWINGS

The foregoing and other features of the present invention will become apparent to one skilled in the art upon a consideration of the following description of the invention with reference to the accompanying drawings, wherein:

FIG. 2 is an enlarged view of a back imaging platform of the table of FIG. 1A;

FIG. 3 illustrates the platform of FIG. 2 in a raised condition;

FIG. 4 illustrates the platform of FIG. 2 in a lowered condition;

FIG. 5 is a view similar to FIG. 2 showing a different actuating mechanism for the back imaging platform;

FIG. 6 illustrates the platform of FIG. 5 in a raised condition;

FIG. 7 illustrates the platform of FIG. 5 in a lowered condition;

FIG. 8 is an enlarged view of a knee imaging platform portion of the table of FIG. 1;

FIG. 9 illustrates the platform of FIG. 8 in a raised condition;

FIG. 24 is a top plan view of a shoulder positioning apparatus in accordance with the present invention shown attached to an imaging table with a shoulder coil;

FIG. 25 is a side view of the apparatus of FIG. 24;

FIG. 25A is a partial end view of the positioning apparatus of FIG. 25 taken along line 25A—25A of FIG. 24;

FIG. 34 is an enlarged end view of the hand cuff of the apparatus of FIG. 30;

FIG. 35 is a side view of the hand cuff of FIG. 34;

FIG. 36 is a bottom plan view of the hand cuff of FIG. 34;

FIG. 41 is a schematic view showing the dimensions of a known primary MRI coil;

FIG. 42 is a schematic view showing the dimensions of a larger sized primary MRI coil embodying the present invention; and FIG. 43 is a schematic view of a vertically extending primary MRI coil in accordance with the present invention.

DESCRIPTION OF PREFERRED EMBODIMENTS

Figure 1A:
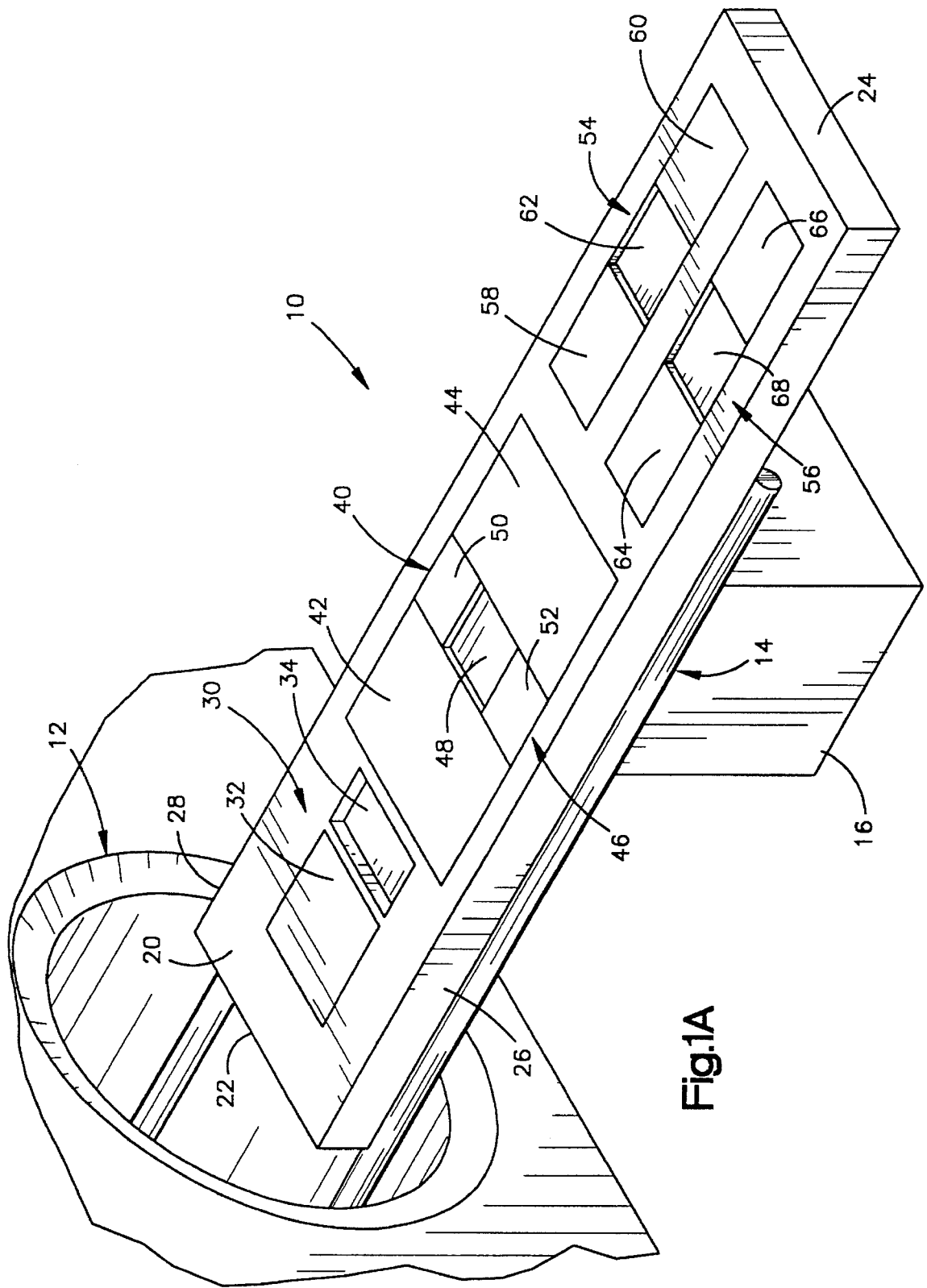
FIG. 1A is a perspective view of a magnetic resonance imaging installation including a patient support table constructed in accordance with the present invention.

FIG. 1A illustrates a patient support table 10 for supporting a patient (not shown) during imaging inside a primary coil 12 of a magnetic resonance imaging installation. The table 10 is supported on tracks 14 and a floor support 16 for sliding longitudinal movement into and out of the coil 12.

The table 10 has an upper major side surface 20 extending between a head end 22 and a foot end 24. The table also has a right side 26 and a left side 28.

The table 10 includes a neck imaging platform indicated generally at 30. The neck imaging platform 30 includes a movable head panel 32 adjacent to a recess 34 for receiving a secondary imaging coil such as a cervical spine coil.

The table 10 includes a back imaging platform indicated generally at 40. The back imaging platform 40 includes a movable upper back panel 42 and a movable lower back panel 44. A movable center section 46 of the back imaging platform 40 includes a recessed panel 48 for receiving a secondary back imaging coil. The recessed panel 48 is located between a left side back panel 50 and a right side back panel 52.

The table 10 also includes a pair of knee imaging platforms 54 and 56. The left knee imaging platform 54 includes a movable upper left knee panel 58, a movable lower left knee panel 60 and, between them, a recessed panel 62 for receiving a left knee secondary imaging coil. Similarly, the right knee imaging platform 56 includes a movable upper right knee panel 64, a movable lower right knee panel 66, and a movable recessed panel 68 for receiving a right knee secondary imaging coil.

Figure 1B:
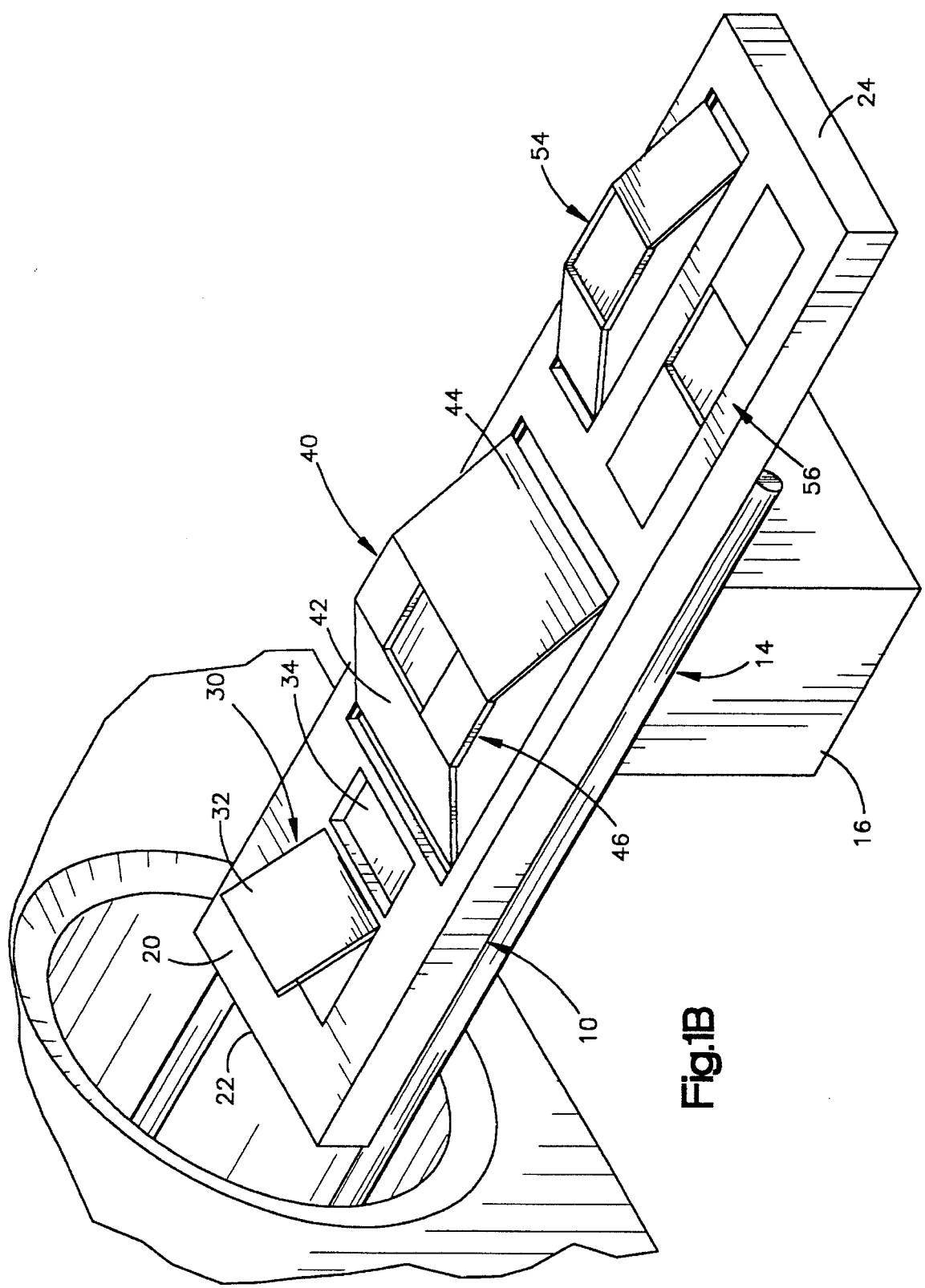
FIG. 1B is a view of the table of FIG. 1A in another condition.
Figure 1C:
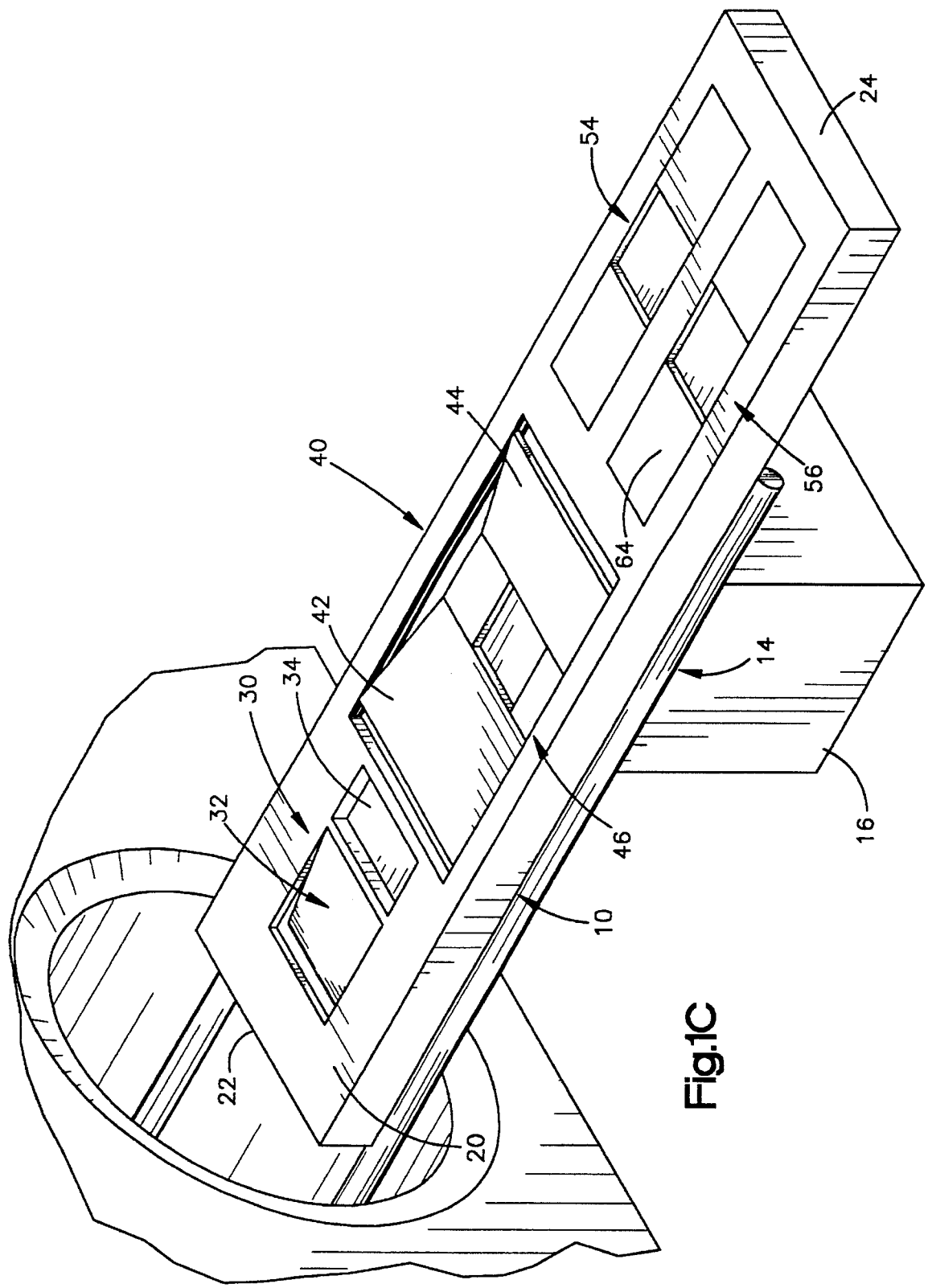
FIG. 1C is a view of the table of FIG. 1A in yet another condition.

As can be seen in FIGS. 1A, 1B and 1C, the head panel 32 is movable between a plurality of positions relative to the upper major side surface 20 of the table 1A. In FIG. 1A, the head panel 32 is in a position level with the upper major side surface 20 of the table 10. In FIG. 1B, the head panel 32 is raised above the upper major side surface 20 of the table 10. In FIG. 1C, the head panel 32 is lowered below the upper major side surface 20 of the table 10. With a patient's head on the head panel 32 and by moving the panel 32 in a manner as described below, a patient's cervical spine can be imaged in a variety of positions, by a coil placed on the recess panel 34.

Similarly, the back imaging platform 40 is movable between a plurality of positions relative to the upper major side surface 20 of the table 10, to image the back in varying positions. In FIG. 1A, the back imaging platform is level or flush with the upper major side surface 20 of the table 10. In FIG. 1B, the back imaging platform 40 is raised up above the upper major side surface 20 of the table 10, in order to hyper-extend the spine of a patient lying on the table 10. In FIG. 1C, the back imaging platform 40 is lowered below the upper major side surface 20 of the table 10, in order to flex the spine. Thus, by moving the back platform 40 between these various positions, in a manner to be described below, the back can be imaged in a plurality of different positions, rather than only in the one flat position possible with a flat table.

Similarly, the left and right knee imaging platforms 54 and 56, respectively, are movable between a plurality of positions relative to the upper major side surface 20 of the table 10. In FIGS. 1A and 1C, the platforms 54 and 56 are illustrated flush with the upper major side surface 20 of the table 10. In FIG. 1B, the left knee imaging platform 54 is illustrated as raised up above the upper major side surface 20 of the table 10. Both knee platforms 56 and 66 are each independently movable above or below the upper major side surface 20 of the table 10. By thus moving a knee platform among these various positions, in a manner to be described below, a knee joint can be imaged in a plurality of positions, as opposed to the one single position available with a flat or nonmovable table.

FIGS. 2–4 illustrate in more detail the back imaging platform 40 and a mechanism for actuating same. These are exemplary of the other platforms and their actuating mechanisms. The fixed portion 70 of the table 10 includes a track 72 receiving mounting rollers 74 and 76 for the upper back panel 42 and lower back panel 44, respectively. The upper back panel 42 is pivotally mounted at 78 to the center back section 46. The lower back panel 44 is similarly pivotally mounted at 80 to the center back section 46.

An inflatable bladder 82 extends between the center back section 46 and the lower panel 84 of the table 10. The inflatable bladder 82 is supplied with fluid through a fluid supply line 86 extending along the table 10. Fluid under pressure, preferably air, is supplied to the bladder 82 through the line 86 by means not shown such as a pump or a high pressure air line as is commonly found in hospitals, etc. Upon inflation of the bladder 82 from the condition shown in FIG. 2 to the condition shown in FIG. 3, the bladder 82 extends longitudinally, raising the center back section 46 of the table 10 upwardly from the major side surface 20 of the table 10. The pivotal connections 74, 76, 78 and 80 allow the panels 42 and 44 to pivot upwardly, as illustrated in FIG. 3, sliding inwardly along the track 72.

Similarly, upon the reduction of pressure in the bladder 82, the bladder 82 compresses axially in length to the condition shown in FIG. 4, lowering the center back section 46 below the major side surface 20 of the table 10. The state of inflation of the bladder 82 is selectively controllable to position the center back section 46, relative to the upper major side surface 20 of the table 10, at any position between the fully extended position illustrated in FIG. 3 and the fully flexed position illustrated in FIG. 4. The bladder 82 is preferably of a bellows—type construction for increased strength and controlled movement.

In FIGS. 2–4, a secondary coil 90 is illustrated as positioned on the center back section 46 of the table 10. The secondary coil 90 may be any known imaging coil designed for imaging a portion of the spine of a patient. As the center back section 46 moves up and down, the secondary coil 90 moves with the back section 46. The secondary coil 90 is initially (FIG. 2) parallel to the upper major side surface 20 of the table 10, and stays with the center back section 46 in that parallel orientation throughout the entire range of movement of the back section 46 and the coil 90. It should be noted that any type of secondary coil either known or to be developed in the future-surface coil, volume coil, etc.—can be used with the present invention.

With a patient (not shown) lying on the table 10, and a secondary coil 90 positioned as shown, the patient's back can be imaged in a plurality of orientations. If the table 10 is maintained in the position shown in FIG. 2, the patient's back is imaged in a flat position. If the table 10 is moved to a raised position, as illustrated in FIG. 3, the patient's back is imaged in an extended or hyper-extended condition. If the table 10 is moved to a lowered condition, as illustrated in FIG. 4, the patient's back is imaged in a flexed or hyperflexed condition. Because the inflation state of the bladder 82 is selectively controllable and lockable at any state of inflation, the patient's back can be imaged when in any selected orientation within the full range of motion of the back imaging platform 40. Meanwhile, the secondary coil 90 moves with the patient's back, always staying in close proximity thereto, to maintain the high resolution sought by use of a secondary coil. Further, the secondary coil 90 always maintains its orientation parallel to the upper side surface 20 of the table 10, as is necessary for maximum resolution and clarity. Accordingly, it is seen that the present invention provides an apparatus for imaging the back of a patient, at any selected one or group of a plurality of orientations, while the patient is maintained in the primary coil 10 (FIG. 1) of the MRI imaging apparatus, and without any extra effort on the part of the patient.

FIGS. 5–7 illustrate an alternate actuating mechanism for the center back section 46 of the table 10. The actuating mechanism includes a threaded rod 100 rotatably mounted in a block 102 fixed to the bottom panel 84 of the table 10. The block 102 allows the rod 100 to rotate but prevents axial movement of the rod 100.

The rod 100 includes a first threaded portion 104 threadedly received in a floating mounting block 106 (FIG. 6). The floating block 106 has a pin 108 secured thereto. The pin 108 is received in a slot 110 of an arm 112 fixed to the upper back panel 42.

The rod 100 also includes a second threaded portion 114 which is of opposite hand from the first threaded portion 104. The second threaded portion 114 extends through a floating mounting block 116 having a pin 118 secured thereto. The pin 118 is received in a slot 120 of an arm 122 fixed to the lower back panel 44.

An end portion 124 of the rod 100 projects axially from the foot end 24 of the table 10. A drive means indicated schematically at 126 is attached to the rod 100. The drive means 126 may be a hand crank for rotating the rod 100 relative to the table 10. The drive means 126 may also be an electric motor or fluid drive mechanism for rotating the rod 100. The drive means 126 is selectively controllable to rotate the rod 100 to any given extent permitted by the actuating mechanism.

Upon actuation of the drive means 126, the rod 100 rotates relative to the fixed mounting block 102 and the table 10. Because the threaded rod portions 104 and 114 are of opposite hand, upon rotation of the rod 100 in one direction, the floating blocks 106 and 116 are moved inwardly toward each other as illustrated in FIG. 6; and upon rotation of the rod 100 in the opposite direction, the blocks 106 and 116 move axially outwardly away from each other, as illustrated in FIG. 7.

Upon movement of the blocks 106 and 116 toward each other as illustrated in FIG. 6, the pins 108 and 118 pull the arms 112 and 122, respectively, from the position shown in FIG. 5 to the position shown in FIG. 6. This causes the upper and lower back panels 42 and 44, respectively., to pivot and move inwardly along the track 72. This raises the center back section 46 of the table 10 upwardly away from the major side surface 20 of the table 10. The surface coil 90, as before, moves with the center back section 46 and maintains its alignment parallel to the upper major side surface 20 of the table 10.

Upon rotation of the rod 100 in the opposite direction, the blocks 106 and 116 (FIG. 7) move axially outwardly away from each other, thus causing the panels 42 and 44 to pivot to the position shown in FIG. 7. This drops the center back section 46 downwardly below the upper major side surface 20 of the table 10, taking with it the secondary coil 90.

Accordingly, it is seen from FIGS. 5–7 that an alternate mechanism for positioning the center back section 46 of the table 10, relative to the upper major side surface 20 of the table 10, is provided. With a patient lying on the upper major side surface 20 of the table 10, the patient's back may thus be imaged in any selected one of a plurality of positions between flexion and extension. Meanwhile, the secondary coil 90, if used, moves with the patient's back to maintain high resolution, while maintaining its planar orientation relative to the upper major side surface 20 of the table 10.

FIGS. 8 and 9 illustrate operation of the right knee imaging platform 56 of table 10. In this case, a knee secondary coil 130 is fixed by suitable means such as straps or VELCRO® to the central panel 68 of the imaging platform 56. The central panel 68 is pivotally mounted between the upper right knee panel 64 and the lower right knee panel 66. A threaded rod 132, having oppositely threaded portions 134 and 136, is rotatably mounted in a fixed mounting block 138 to block axial movement of the rod 132. Connection means 140 (similar to the block 106, pin 108, and arm 112) movably connects the upper right knee panel 64 to the threaded rod portion 134. Similar connection means 142 movably connects the lower right knee panel 66 to the rod threaded portion 136.

Upon rotation of the rod 132 by suitable drive means 144, in one direction, the connection means 140 and 142 cause the panels 64 and 66, respectively, to pivot and lift the central panel 68 upwardly away from the upper major side surface 20 of the table 10. The knee coil 130 moves with the panel 68 and stays in the correct planar orientation relative to the primary coil. The patient's knee (not shown.) also moves upwardly away from the major side surface 20, into a different orientation than when the patient's knee is on the platform 56 when in the position shown in FIG. 8. Rotation of the rod 132 in the opposite direction causes the central panel 68 and knee coil 130 to drop below the upper major side surface 20 of the table 10, in a manner similar to that illustrated in FIG. 7 with the back section 46.

Figure 10:
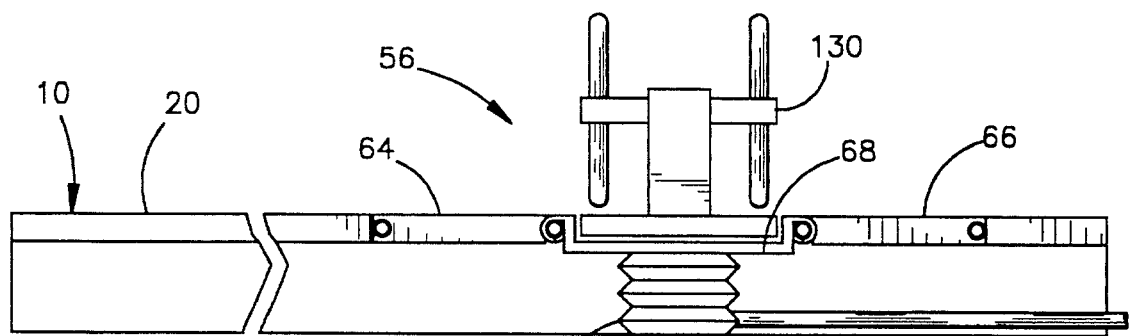
FIG. 10 is a view similar to FIG. 8 and showing a different actuating mechanism for the knee platform.
Figure 11:
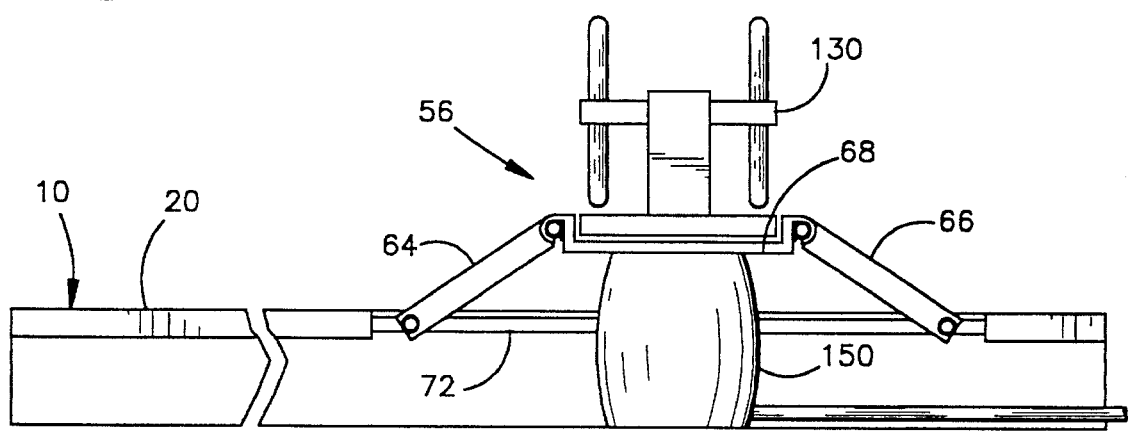
FIG. 11 illustrates the platform of FIG. 10 in a raised condition.

In the structure illustrated in FIGS. 10 and 11, the rod 132 and associated actuating mechanism are replaced by an inflatable bladder 150. The bladder 150 is supplied with fluid under pressure through suitable means (not shown). Upon inflation of the bladder 150 from the normal state illustrated in FIG. 10 to the extended state illustrated in FIG. 11, the panel 68 and the knee coil 130 are again raised above the upper major side surface 20 of the table 10. Upon the reduction of pressure in the bladder 150, the bladder 150 collapses axially to lower the panel 68 below the major side surface 20 of the table 10. Thus, the knee joint can also be imaged in a hyper-extended condition.

Figure 12:
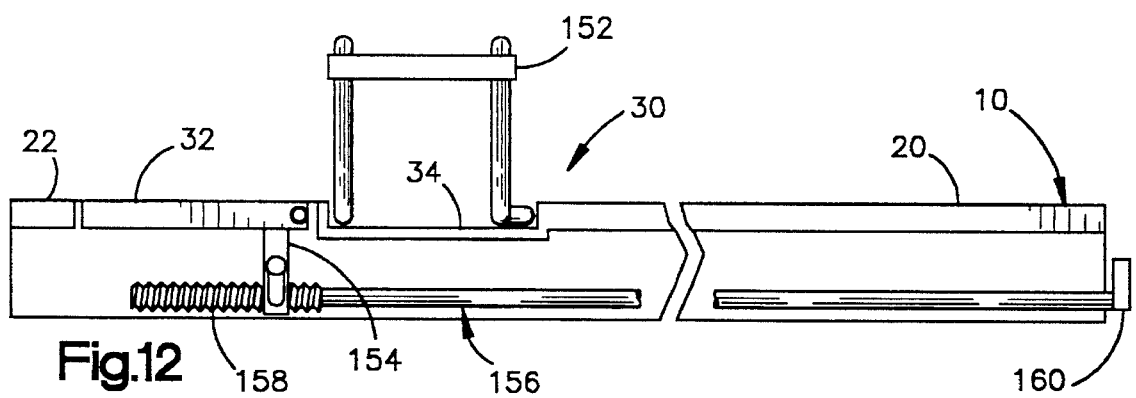
FIG. 12 is an enlarged view of a neck imaging platform portion of the table of FIG. 1A.
Figure 13:
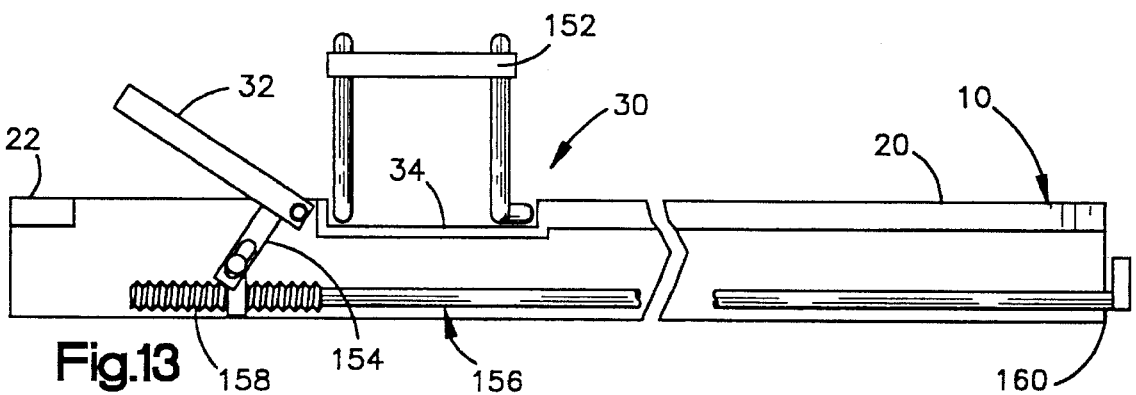
FIG. 13 illustrates the platform of FIG. 12 in a raised condition.
Figure 14:
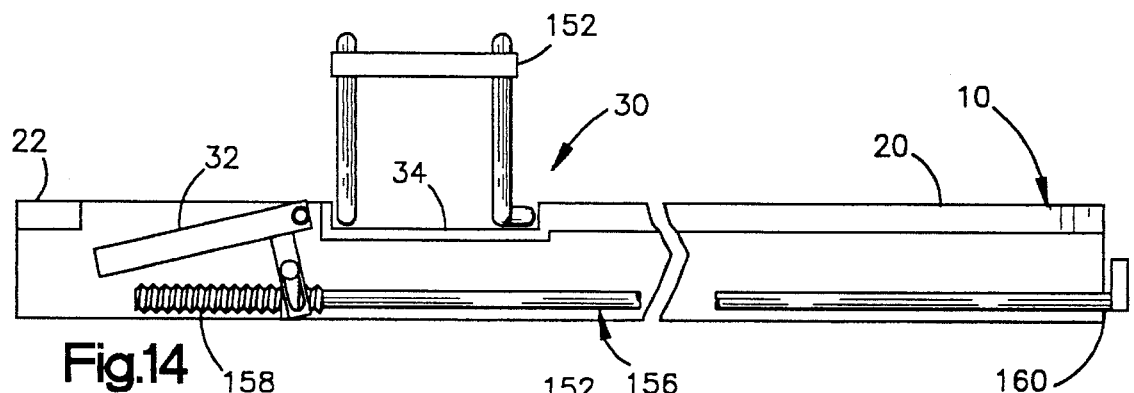
FIG. 14 illustrates the platform of FIG. 12 in a lowered condition.

FIGS. 12, 13 and 14 illustrate operation of the neck imaging platform 30 of the table 10. A cervical spine coil 152 is set in the recessed panel portion 34 of the table 10, below the upper major side surface 20. Attached to the head panel 32 is a pivot mechanism 154. A rod 156 has a threaded portion 158 extending through the mechanism 154. Upon rotation of the rod 156 by a suitable drive means 160, the actuating mechanism 154 causes the head panel 32 to pivot upwardly out of the plane of the major side surface 20 of the table 10, from the position shown in FIG. 12 to the position shown in FIG. 13. The panel 32 can be lowered below the major side surface 20 of the table 10 by rotation of the rod 156 in the opposite direction.

With a patient's head lying on the panel 32 and the patient lying on the surface 20 of the table 10, movement of the panel 32 relative to the upper major side surface 20 of the table 10 causes flexion and extension of the patient's cervical spine. With the cervical spine coil 152 disposed about the cervical spine of the patient, the patient's cervical spine can be imaged in any selected one of a plurality of positions throughout the range of movement of the panel 32. Thus, rather than being limited to one image of the cervical spine while the patient is lying flat on an imaging table, the physician can obtain multiple images of the cervical spine at various positions throughout its range of motion. This is possible with any of the moving parts of the body which can be imaged. For example, movement can be measured and controlled in degrees—move a joint 5°, image, move the joint 5° further, image again, etc. Motion can also be measured in distances such as centimeters between positions.

Figure 15:
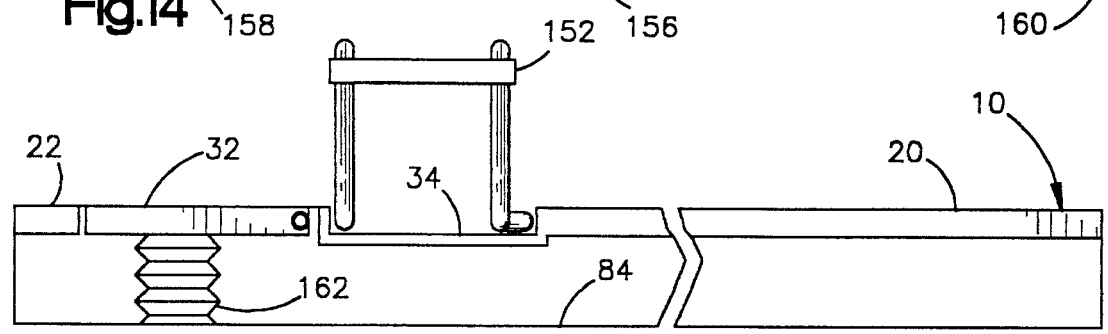
FIG. 15 is a view similar to FIG. 12 illustrating a different actuating mechanism for the neck platform.
Figure 16:
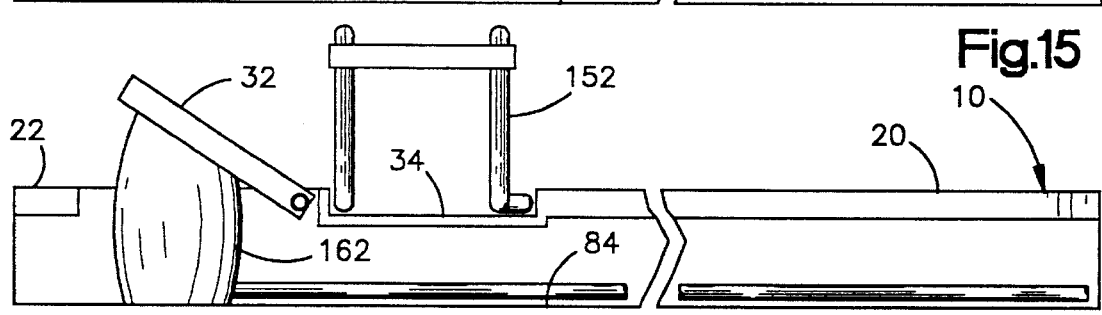
FIG. 16 illustrates the platform of FIG. 15 in a raised condition.
Figure 17:
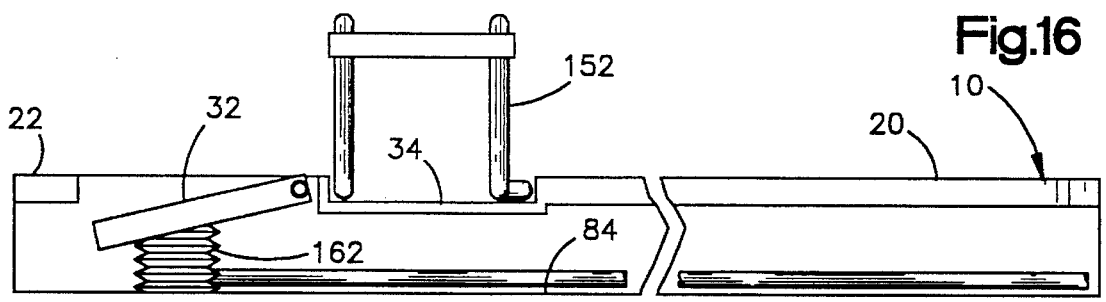
FIG. 17 illustrates the platform of FIG. 15 in a lowered condition.

FIGS. 15–17 illustrate an alternate mechanism for raising and lowering the panel 32. An inflatable bladder 162 is fixed between the head panel 32 and the bottom panel 84 of the table 10. When the bladder 162 is in its neutral condition, the panel 32 is flush with the upper major side surface 20 of the table 10. When the bladder 162 is inflated, the panel 32 is raised upwardly, out of the upper major side surface 20, to the elevated position illustrated in FIG. 15. When the bladder 162 is deflated, the panel 32 is lowered below the upper major side surface 20 to the depressed position illustrated in FIG. 16. Again, by controlling the pressure in the bladder 162, the MRI operator can fix the head panel at any given position within its range of motion, in order to image the cervical spine at a selected degree or flexion of extension.

Figure 18:
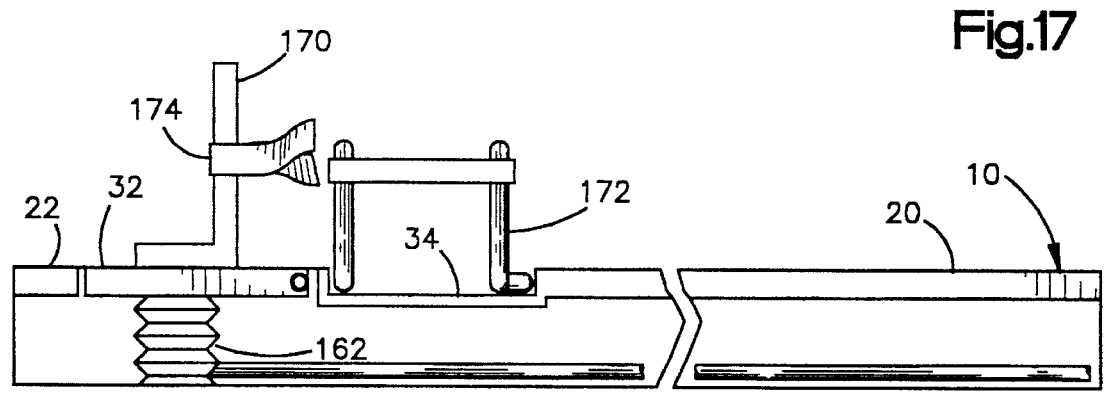
FIG. 18 illustrates the platform of FIG. 15 with a foot rest attached for use in ankle imaging.
Figure 19:
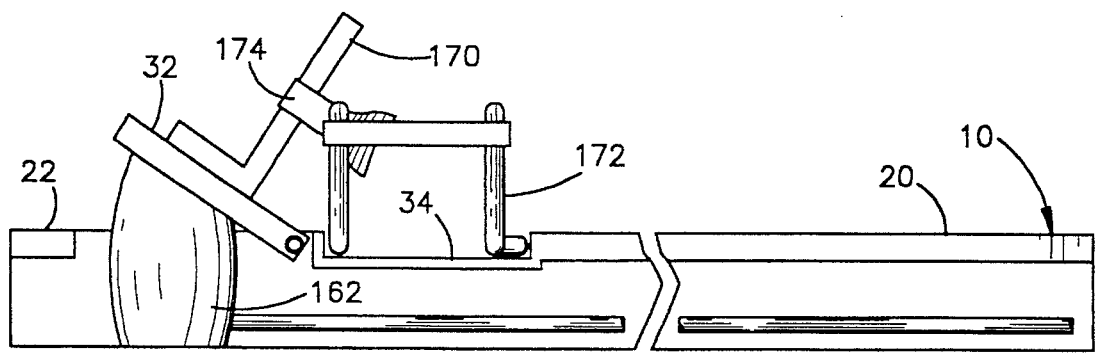
FIG. 19 illustrates the platform of FIG. 18 in a raised condition.
Figure 20:
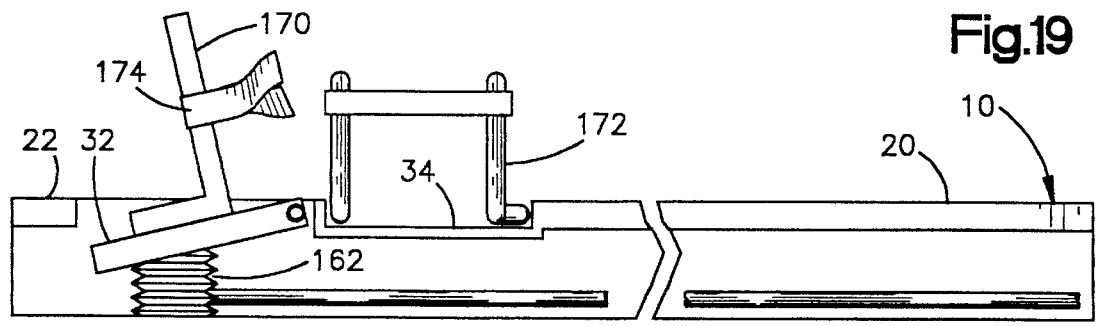
FIG. 20 illustrates the platform of FIG. 18 in a lowered condition.

FIGS. 18–20 illustrate the use of the neck imaging platform as modified for imaging an ankle of a patient (not shown). The head panel 32 is modified by the addition of a foot rest 170. The foot rest 170 is secured to the panel 32 by suitable means. The patient lies on the table 10 with, instead of his head at the head end 22, his feet toward that end. The bottom of the patient's foot is positioned against the foot rest 170, with the ankle over the recessed panel 34. An ankle imaging coil 172 is placed over the ankle. A strap 174 secures the patient's foot to the foot rest 170.

When the bladder 162 is in the neutral condition illustrated in FIG. 17, the patient's ankle is in a normal position and may be imaged. Upon further inflation of the bladder 162, the panel 32 raises upwardly away from the major side surface 20 of the table 10. The footrest 170 bends the patient's ankle and the ankle may then be imaged with the coil 172 in that bent condition. Upon the application of suction or lowering of pressure to the bladder 162 (FIG. 20), the panel 32 is pivoted down below the major side surface 20 of the table 10, thus bending the ankle in the opposite direction. The ankle may be imaged in that opposite direction with the secondary coil 172.

Figure 21:
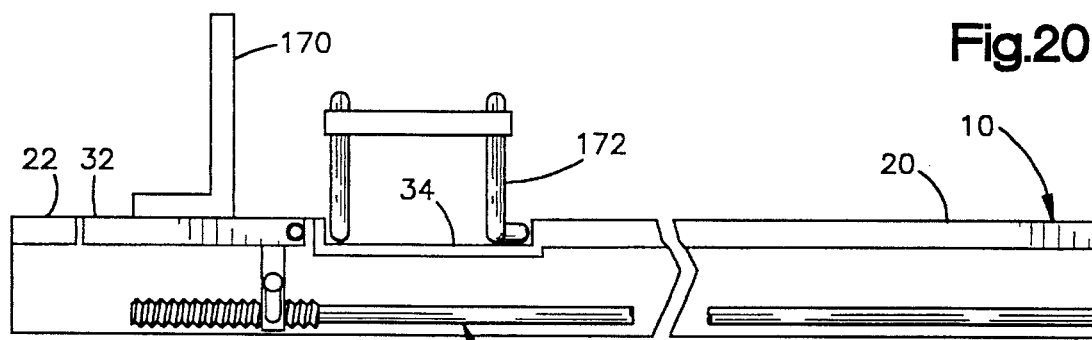
FIG. 21 illustrates the platform of FIG. 18 with a different actuating mechanism.
Figure 22:
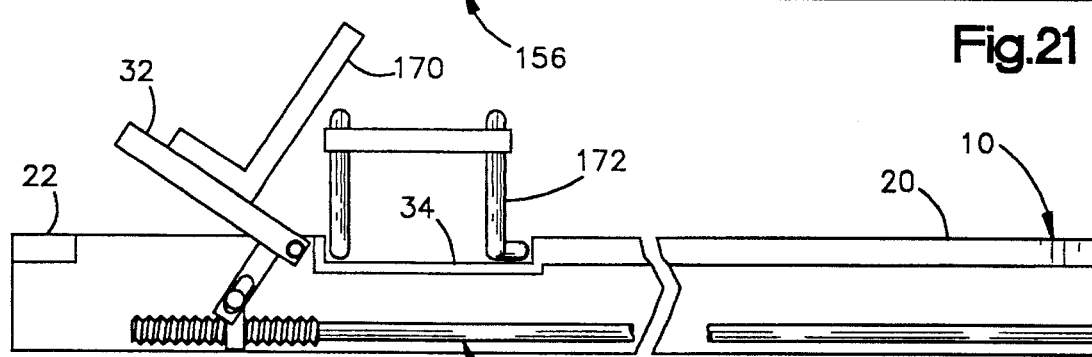
FIG. 22 illustrates the platform of FIG. 21 in a raised condition.
Figure 23:
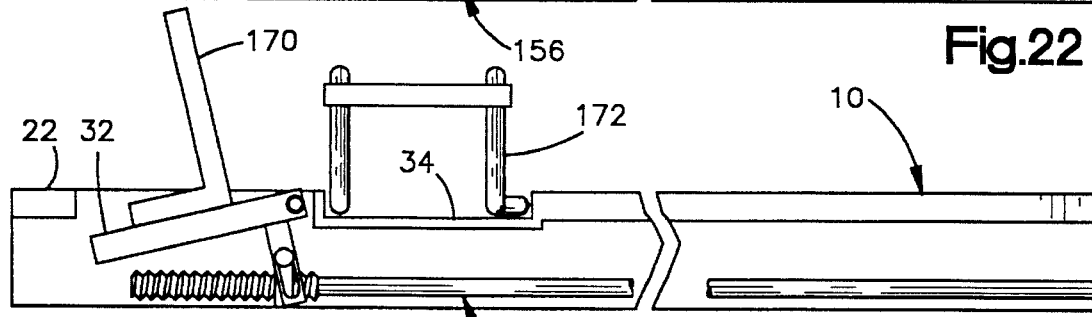
FIG. 23 illustrates the platform of FIG. 21 in a lowered condition.

FIGS. 21–23 illustrate an alternate actuating mechanism for the ankle imaging platform of FIGS. 17–19. The actuating mechanism is like the actuating mechanism illustrated in FIGS. 12 and 13 for use of the panel 32 in cervical spine imaging. Upon rotation of the rod 156 in one direction or the other, the panel 32 and footrest 170 are pivoted either above the major side surface 20 of the table 10, or below the surface 20, to position the ankle for imaging at any selected position within its range of motion. It should be understood that a separate movable portion of the table 10 could be provided for use in ankle imaging, rather than using the neck imaging platform 30.

It should also be understood that a table in accordance with the present invention need not include every specific movable platform as shown herein. Rather, such a table may include only one movable platform, or any combination of various movable platforms. It should further be understood that suitable control means is provided for moving the several platforms, in a known manner, in order to provide repeatable movement of the various platforms through their respective ranges of motion, in order to provide repeatable imaging at known positions. The table can also be used, of course, for other types of imaging such as ultrasound or CAT scans. It should further be understood that any of the platforms may be provided as separate devices which can be placed atop a known imaging table, rather than being built into a new table as shown.

Accordingly, it is seen that the present invention provides an imaging table for positioning a body part so as to control the position or orientation of the body part. This positioning is independently controllable by the operator from a location external to the primary coil. This positioning requires no physical support effort by the patient during the time period of the imaging to maintain the selected position, as the table fully supports the weight of the body part connected therewith. Accordingly, a plurality of sequential images may be taken of a joint, for example, in differing positions, without undue effort on the part of the patient.

Figure 26:
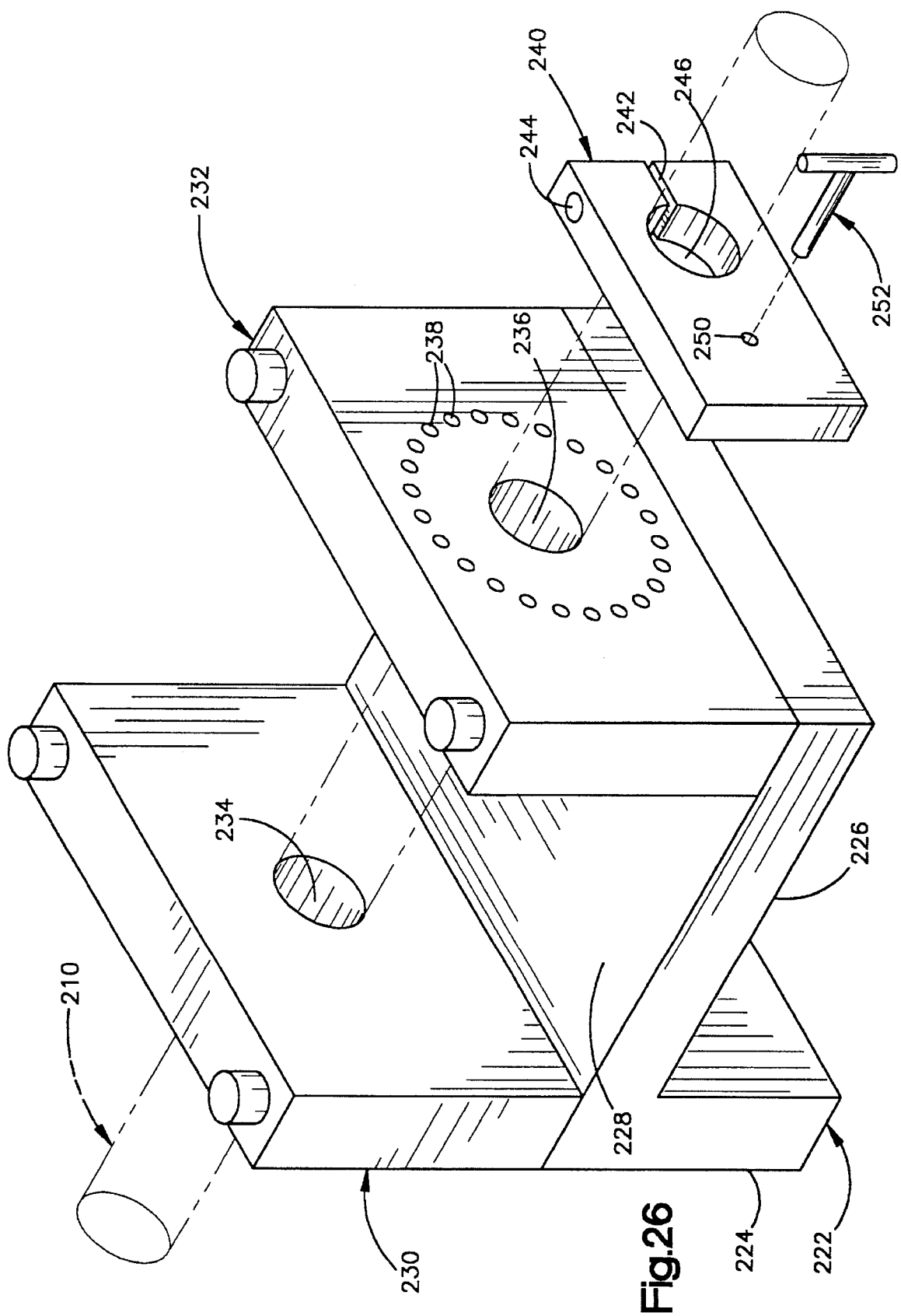
FIG. 26. is an enlarged perspective view of a portion of the positioning apparatus of FIG. 24.

In another embodiment of the invention, FIGS. 24–26 illustrate an apparatus 200 for positioning a body part within a primary imaging coil. The apparatus 200 is mounted to an imaging table 202 which may be the imaging table 10 or may be a known imaging table. A known secondary imaging coil 204 is secured to the table 202 by suitable means. The coil is located in a position for imaging a particular body part. As illustrated in FIGS. 24 and 25, the coil 204 is positioned to image a shoulder of a patient who is lying on the table 202 with his head adjacent the end 206 of the table 202.

The apparatus 200 includes a support rod 210 extending longitudinally along the table 202 from a position over the table 202 (inside the primary coil) to a position off the end of the table 202 (outside the coil). The rod 210 has an inner end portion 212 to which is fixed an attachment member 214. The member 214 may be any suitable structure such as a cuff for attachment to a body part such as a forearm, for example, and may include means (such as the strap 5215) for securing the cuff to the body part for movement therewith. The rod 210 also has an outward end portion 216 to which is attached a handle 218 for rotational and longitudinal movement of the rod 210 by a person other than the patient (not shown).

The rod 210 extends through and is positioned by an index mechanism 220, better seen in FIG. 26. The index mechanism 220 includes a base 222 having a first leg portion 224 and a second leg portion 226. The leg portion 224 is fixed to the table 202. The leg portion 226 has an upper major side surface 228 to which are attached support blocks 230 and 232. The support block 230 has an opening 234 through which the rod 210 extends and is movable. The support block 232 has an opening 236, aligned with the opening 234, through which the rod 210 also extends and is movable. The blocks 230 and 232 support the rod 210, and thus the cuff 214. The block 232 also has a plurality of index openings 238. The index openings 238 are spaced regularly in a circle around the rod 210.

An index block 240 is disposed on the rod 210 outside the block 232. The rod 210 extends through an opening 246 in the index block 240. The index block 240 includes a split clamp portion 242 and a clamping bolt 244. When the split clamp 242 is loosened, the index block 240 is rotatable on and movable longitudinally on the rod 210. When the split clamp 242 is tightened, the block 240 is fixed for movement with the rod 210.

The index block 240 has an index pin opening 250 through which is extensible an index pin 252. The opening 250 is the same distance from the center of the opening 246, as the index openings 238 are from the center of the opening 236 in the block 232. Thus, the index pin opening 250 is alignable with any selected one of the index openings 238 on the support block 232. When the opening 250 is aligned with one of the index openings 238, the index pin 252 maybe inserted through the index pin opening 250 and into the selected index opening 238, to block rotation of the index block 240 relative to the support block 232. If the index block 240 is clamped firmly to the rod 210, this blocks rotational movement of the rod 210 relative to the support block 232. Since the support block 232 is fixed to the table 202, this therefore blocks rotational movement of the rod 210 relative to the table 202, also thus fixing the cuff 214 in position. Further, when the index pin 252 is extended through the index pin opening 250 and into one of the index locations 238, the index assembly 220 blocks longitudinal movement of the rod 210 relative to the table 202. Thus, the cuff 214 is completely fixed in position relative to the table 202 and the coil 204.

Figure 26A:
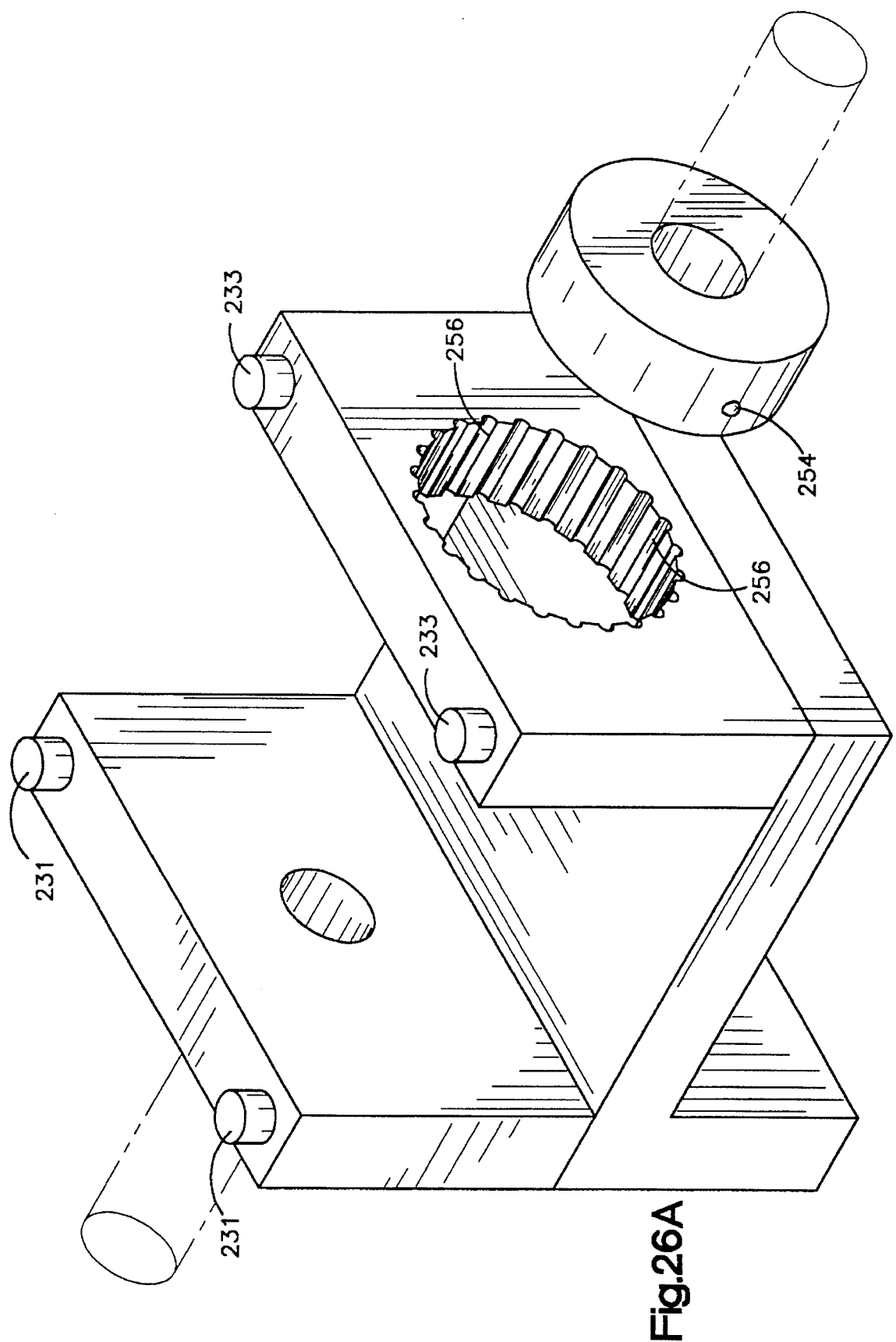
FIG. 26A is a view similat to FIG. 26 showing an alternate indexing mechanism.

It should be noted that other indexing mechanisms may be provided to replace the index pin opening 250 and index pin 252. For example, as shown in FIG. 26A, the index block 240 may have a spring loaded ball 254 on its radially outer surface facing the support block 232, which is selectively engageable at one of a plurality of ribbed index locations 256, thus functioning as a detent mechanism. This is suitable for a patient-directed operation. If the apparatus 200 is to be patient directed, the portion of the rod 210 extending outwardly past the index mechanism 220 may be omitted. The patient adjusts the index mechanism by moving the body part, thus moving the cuff and support rod. Other index constructions are equally feasible.

In operation of the positioner apparatus 200, the patient is first placed on the table 202 in a position as desired. The coil 204 is adjusted so as to properly image the body part in question. (It should be noted that use of a secondary coil such as the coil 204 is not essential to functioning or use of the apparatus 200.) The cuff 214 is then attached to a portion of the patient's body at a location selected to be able to move the body part to be imaged into a plurality of different positions. For example, if a shoulder joint is to be imaged, then the cuff 214 may be attached to the patient's forearm. Movement of the patient's forearm by means of the rod 210 will then cause the shoulder joint to move between a plurality of different positions. Similarly, if the patient's hip is to be imaged, the cuff 214 may be attached to the patient's leg, for example, the lower leg. Movement of the cuff 214 will cause movement of the hip joint to a plurality of different positions in which it may be sequentially imaged.

The rod 210 as noted is longitudinally movable by pulling or pushing on the handle 218. Thus, as the imaging operator moves the handle 218 longitudinally relative to the table 202, the cuff 214 thus moves longitudinally also. The operator can therefore control the longitudinal position of the cuff 214, and of its attached body part, from a location exterior to the primary coil.

The rod 210 is also rotatable, by means of the handle 218. The operator rotates the handle 218 to position the cuff 214 and its attached body part in the desired orientation for imaging. This rotational position is then locked in by means of the index assembly 220. It should be noted that any number, location, or sequence of index locations 238 may be provided. Those shown are illustrative only. In fact, an index assembly may be provided which can be locked in any rotational position within a full circle.

Many joints are movable in multiple degrees of freedom. The shoulder joint, for example, is movable in four degrees of freedom (or multiple planes of movement). In order to fully understand the joint anatomy, it is desirable to be able to image a joint in all these possible positions. Accordingly, the present invention provides for movement of a positioning apparatus such as the cuff 214 not merely rotationally and longitudinally, but also up and down and sideways.

Thus, as seen in FIGS. 24–26, the apparatus 200 may be made movable up and down and also sideways relative to the table 202. The index blocks 230 and 232 are movable up and down along rods 231 and 233, respectively, which rods are fixed to the base block 222. Thus, the support rod 210 and cuff 214 can be moved up and down to provide a third degree of movement in addition to the rotation and longitudinal movement available. Further, the index assembly 220 has a guide member 235 engaging in a slot 237. Thus, the index assembly is movable sideways along the table 202 to carry the support rod 210 and the cuff 214 in a fourth degree of movement. With these multiple degrees of movement, in multiple planes, it is now possible to move a joint into almost any position to simulate natural joint movement, while within an imaging coil.

Another feature of the present invention is that traction can be applied to a joint being imaged, in order to distract the joint. For example, in the apparatus illustrated in FIGS. 24–26, traction can be applied to a joint by pulling outwardly (to the right as viewed in FIG. 24) on the rod 210. Such force when applied to the rod 210 acts through the cuff 214 on the joint being imaged. Distracting a joint can allow a better view of the parts of the joint and thus an increased imaging benefit. This feature is not available with present imaging apparatus.

It should be noted that additional body part attachments are possible in order to better control movement and positioning. For example, extra cuffs or clamps, in addition to the one cuff shown in the drawings, may be attached to the body to more carefully and tightly control its movement and positioning. Further, it should be understood that other types of cuffs may be used, such as inflatable cuffs, etc. The cuffs should further be designed so that there is no plastic in contact with the skin. Such contact causes sweating and perspiration build up which causes imaging aberrations. Accordingly, a material is preferably provided against the skin to wick the perspiration away.

Accordingly, it is seen that the present invention provides an apparatus for longitudinally and rotationally positioning a body part so as to control the position or orientation of a joint connected with the body part. This positioning is independently controllable by the operator from a location external to the primary coil. This positioning requires no physical support effort by the patient during the time period of the imaging, since the rod positioning apparatus fully supports the weight of the body part connected therewith. Nor does this adjustable positioner require any effort on the part of the patient to maintain the selected position, as the apparatus 200 performs that function also. A plurality of sequential images may be taken of a joint, for example, in differing positions, without undue effort on the part Of the patient. (It should be noted that patient control of any of the positioning apparatus of the present invention is possible, as well as the described operator control.)

Figure 27:
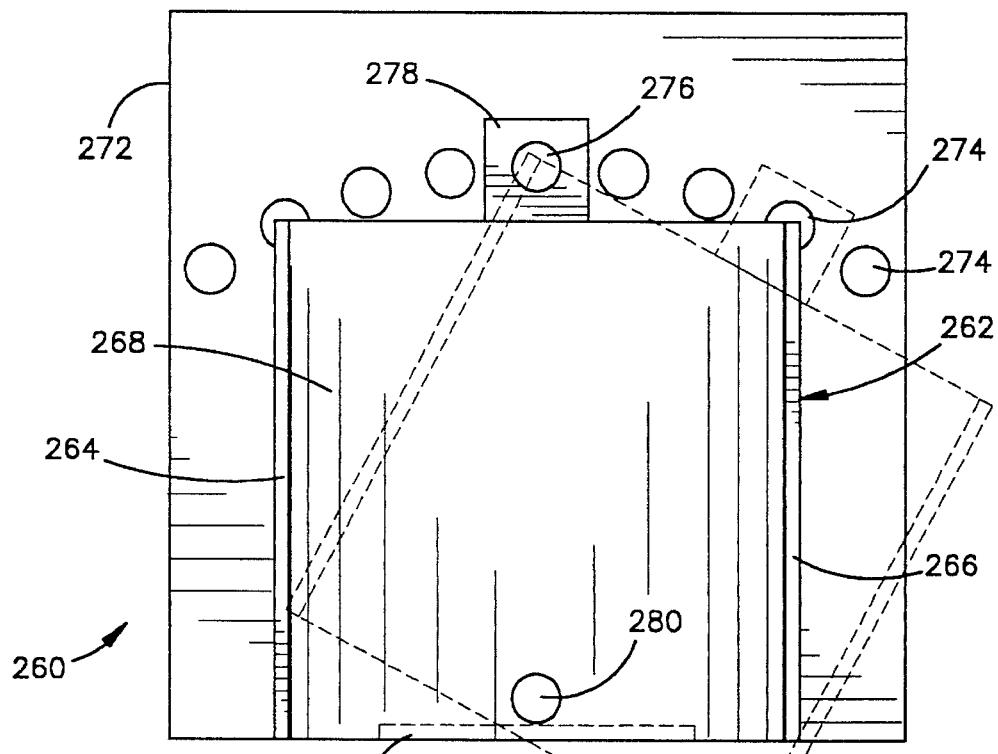
FIG. 27 is a top plan view of a head and neck positioning apparatus.
Figure 28:
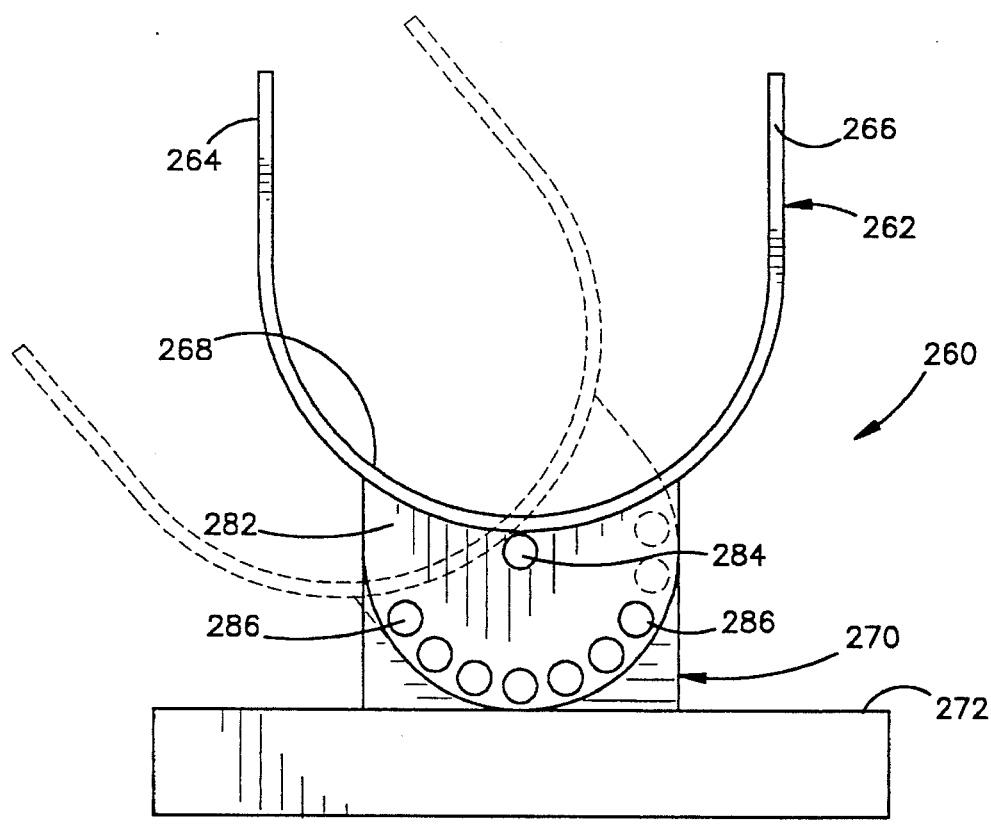
FIG. 28 is an end view of the apparatus of FIG. 27.
Figure 29:
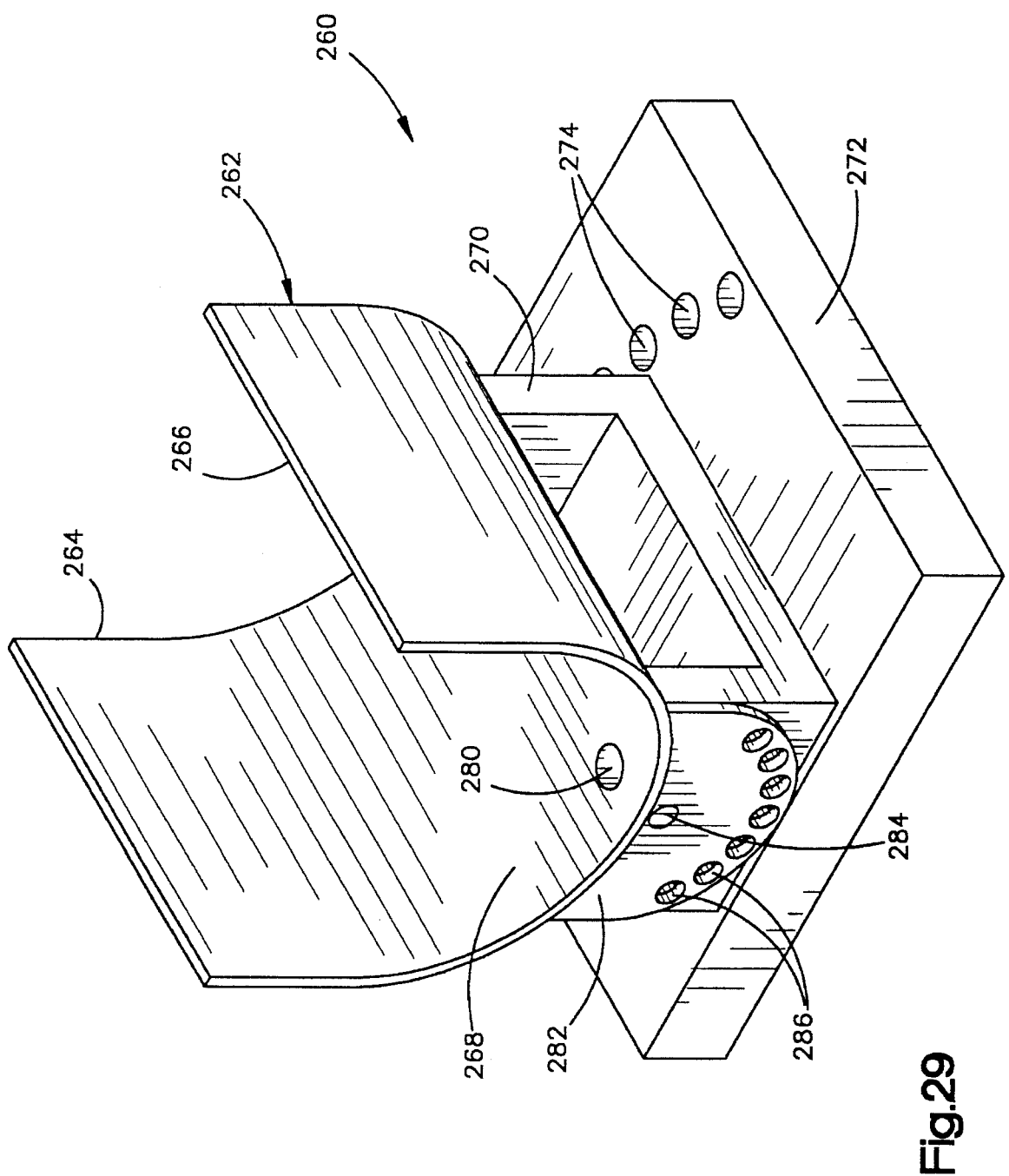
FIG. 29 is a perspective view of the apparats of FIG. 27.
Figure 30:
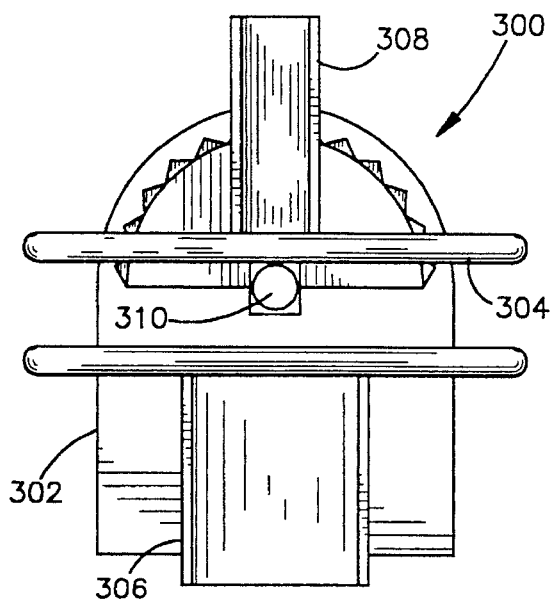
FIG. 30 is a top plan view of a wrist imaging apparatus embodying the present invention and including a hand cuff.
Figure 31:
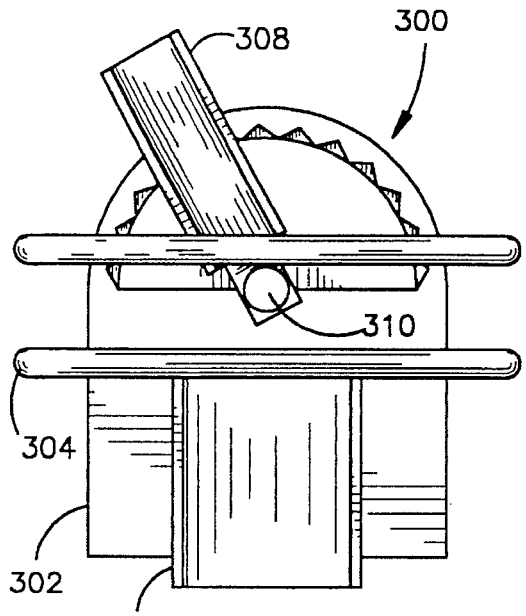
FIG. 31 illustrates the apparats of FIG. 30 in a different condition.

FIGS. 27–29 illustrate another body part positioner having two degrees of movement. An apparatus 260 includes a saddle 262 having upstanding side portions 264 and 266 joined by a bottom portion 268. The saddle 262 is mounted on a base block 270. The base block 270 is mounted on a panel 272 which may be the head panel 32 of the table illustrated in FIG. 1A. The panel 272 has a plurality of index openings 274. An index pin 276 (FIG. 27) extends through a portion 278 of the base block 270 and is receivable in a selected one of the openings 274. The base block 270 is pivotally mounted at 280 to the panel 272. Thus, the base block 270, with its attached saddle 262, may be positioned at a selected one of a plurality of rotational positions relative to the panel 272, as shown in phantom in FIG. 27.

An index plate 282 is attached to the saddle 262. The index plate 282 and saddle 262 are pivotally mounted at 284 to the base block 270. The index plate 282 has a plurality of index openings 286 spaced in an arc about the pivot mounting 284. A locator opening (not shown) is located behind the index plate 282, in the base block 270. The saddle 262, with its attached index plate 282, may be pivotally rotated about the mounting 284, as shown in phantom in FIG. 28, and secured in a position by insertion of an index pin (not shown) through the selected opening 286 into the locator opening in the base block 270.

In operation of the positioning assembly 260, the patient's head is secured in the saddle 262. The saddle 262 and base block 270 are then swung around the pivot axis 280 and locked in a selected position with the index openings 274. The saddle 262 is also rotated, with the index plate 282, about the pivot axis 284 and locked in a selected position. The patient's head or cervical spine is then imaged. The apparatus 260 is then adjusted to a different condition, moving the patient's head or spine to a new position. The patient's head or spine is then imaged again.

Accordingly, it is seen that a patient's head or cervical spine, when the head is in the saddle 262, can be selectively positioned in any one of a plurality of different orientations within two separate degrees of motion. Further, if the head panel 272 is pivotally mounted to the table 10, the attached saddle 262 may also be moved up and down out of the plane of the table, thus moving the patient's head in the saddle 262 in yet a third degree of motion. The control of all these movements may be automated with a fluid drive or other means, may be made remotely controllable from a location outside the coil, or may be patient directed.

Accordingly, it is seen that the present invention also provides apparatus for positioning a body part of a patient for imaging in a plurality of different degrees of motion. For example, the patient's cervical spine may be imaged in a sequence of images by moving the saddle 262 in the desired direction within the various degrees of motion and locking it in place at each selected position. There is no need for the patient to hold any selected position, as the positioning apparatus 260 does this for him. Accordingly, the imaging process is made significantly more stable and more comfortable for the patient.

Because coil support panels such as the recessed panels 34 and 48 (FIG. 1A) are located below the upper major side surface 20 of the table 10, a flat surface coil placed therein will not interfere with normal body positioning. Thus, it is seen that recessing the coils, itself, provides a significant benefit.

Several patient directed devices are illustrated in FIGS. 30–40. Such devices can be part of a new imaging table as described above, but can also be independent, that is, add-ons to an existing imaging table (as the apparatus 200 is an add-on to the table 202 in FIGS. 24–26). They are therefore less expensive and more widely usable.

These patient-directed devices can be end-mounted fixtures such as a modification of those shown in FIGS. 24–26. They can also be fixtures mounted to the upper surface of the table, in effect replacing the movable platforms of the table of FIG. 1A.

Figure 32:
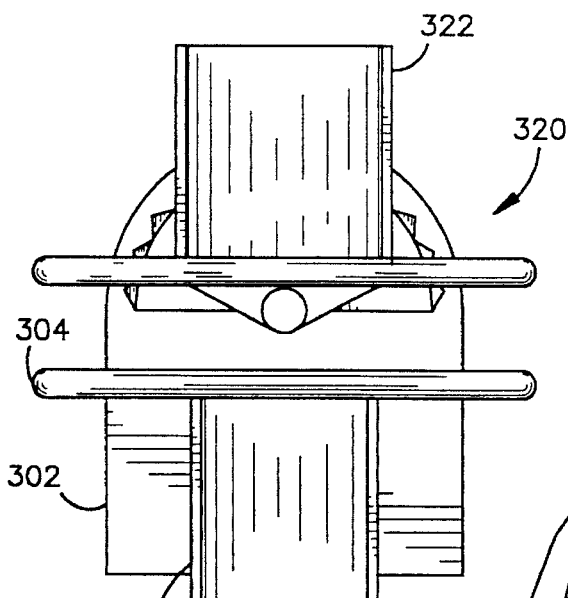
FIG. 32 illustrates the apparatus of FIG. 30 with a different hand cuff.
Figure 33:
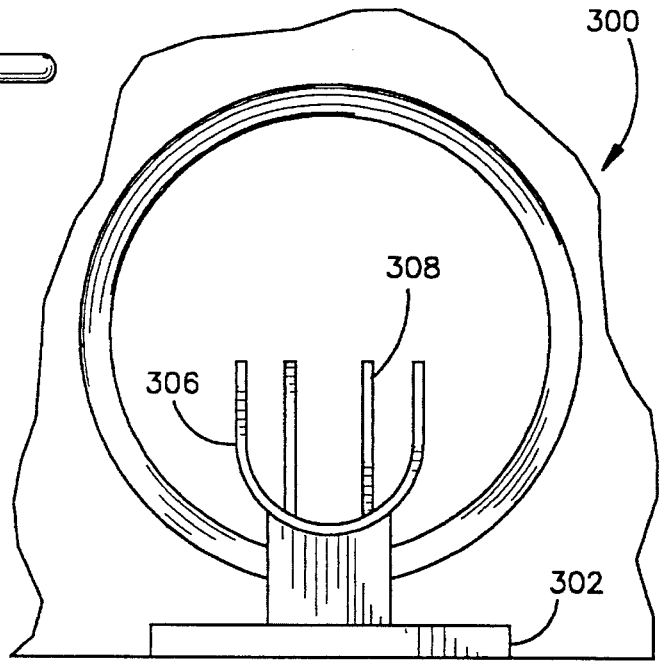
FIG. 33 is an end view of the apparatus of FIG. 30.
Figure 37:
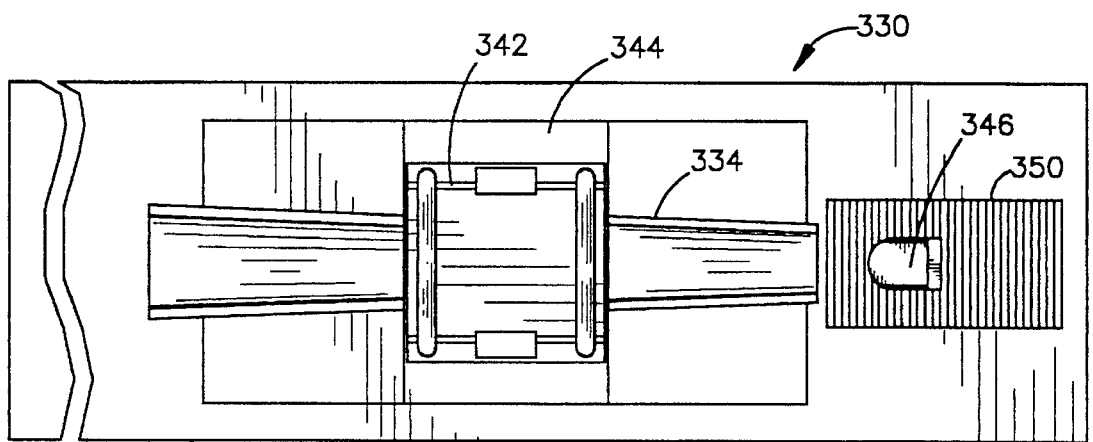
FIG. 37 is a top plan view of an independent patient directed knee positioning apparatus embodying the present invention.
Figure 38:
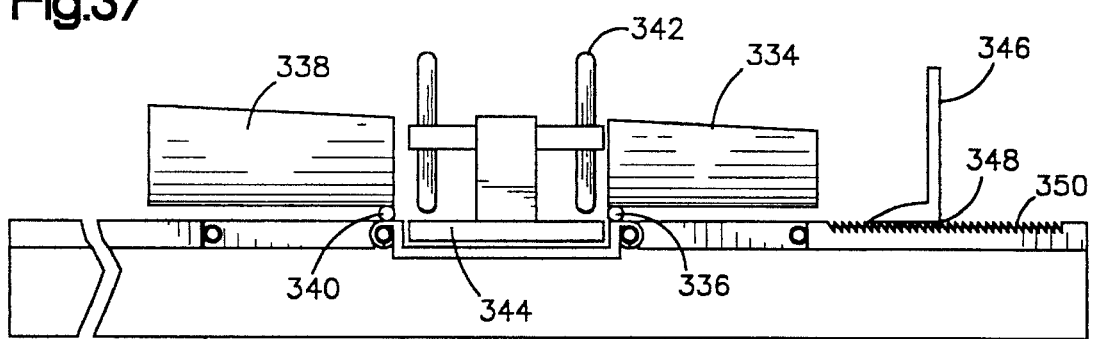
FIG. 38 is a side view of the apparatus of FIG. 37.
Figure 39:
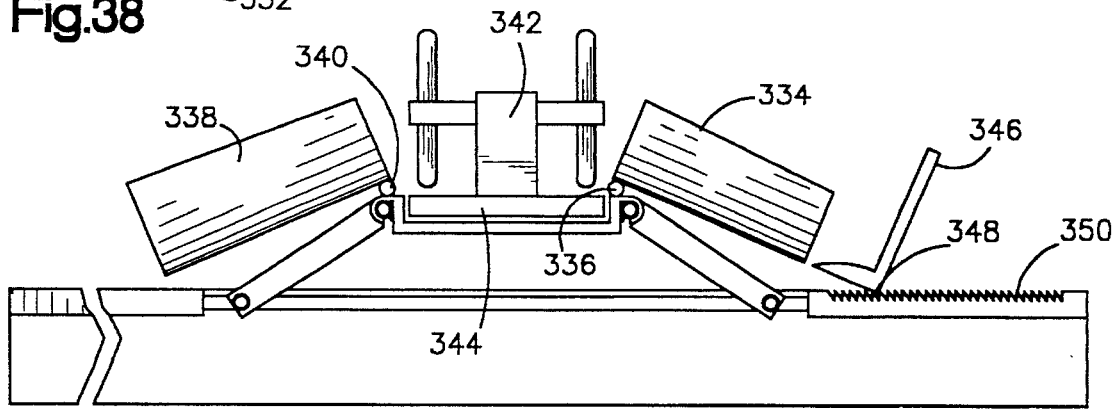
FIG. 39 is a view similar to FIG. 38 with the apparatus in a raised condition.

FIGS. 30–36 illustrate a patient directed wrist movement apparatus 300. The apparatus 300 includes a base 302 which may be secured to an imaging table with suitable means not shown. The base 302 supports an imaging coil 304. The patient's forearm is placed on a forearm cuff 306 secured to the base 302. The patient's hand is placed, thumb up as seen in FIG. 33, in a hand cuff 308. The hand cuff 308 is pivotally mounted at 310 to the base 302. A detent member 312 is located on a lower end portion 314 of the hand cuff 308. The detent member 312 is engageable with a ratchet-type mender 316 on the base 302. Thus, the hand cuff 308 and the base 302 are releasably interlockable at a plurality of positions within their range of rotational movement.

To adjust the apparatus 300, the patient simply applies sufficient torque to release the interconnection between the hand cuff 308 and the base 302 and thereby flex or extend his wrist to the next desired position. The apparatus 300 then interlocks at this newly selected position for imaging by the coil 304.

A modification of the apparatus 300 is illustrated in FIG. 32 with an apparatus 320 having a different hand cuff 322. The hand cuff 322 is designed to have the hand lie flat rather than on edge, with the thumb to the side as viewed in FIG. 32. The wrist is again movable through its range of motion, this time being imaged in a position 90° from that shown in FIG. 30.

FIGS. 37–40 illustrate a patient directed knee imaging apparatus 330. The apparatus is similar to the knee platform of the table 10 of FIG. 1A, but is instead designed to be patient directed (actuated) rather than technician or operator directed.

The apparatus 330 includes a base 332. The base 332 rests on the upper major side surface of the table. Suitable means may be provided to secure the base 332 to the table. A lower leg cuff 334 is releasably secured to the lower leg. The cuff 334 is attached at 336 to the base 332 to maintain the same focal point of imaging as the knee is flexed. An upper leg cuff 338 is releasably secured to the upper leg. The upper leg cuff is also attached at 340 to the base 332.

A knee imaging coil 342 is fixed for movement with a movable panel or portion 344 of the base 332. Attached to the patient's foot is a footrest 346 with a pawl member 348. The pawl member 348 engages a ratchet portion 350 on the base 332.

To adjust the device, the patient simply bends his knee to move his foot and thus the pawl member 348 along the ratchet portion 350 from one position to the next. The panel 344 moves in a manner as described above. The patient's foot is then held in that position firmly enough to allow for accurate imaging.

As the patient moves his foot and knee, the secondary coil 342 moves with the knee and generally stays in position relative to the knee. The secondary coil 342 is constrained for movement by the panel 344 so that it stays in the proper planar orientation relative to the primary imaging coil (not shown). As the patient moves his foot and knee, the cuffs 334 and 338 are constrained for proper movement by the mechanisms which attach them to the base 332 in order to maintain the same focal point of imaging as the knee is flexed. The coil 342 stays in close proximity to the knee, moves longitudinally and up and down as the knee moves, and maintains its proper planar orientation throughout its range of motion.

Figure 40:
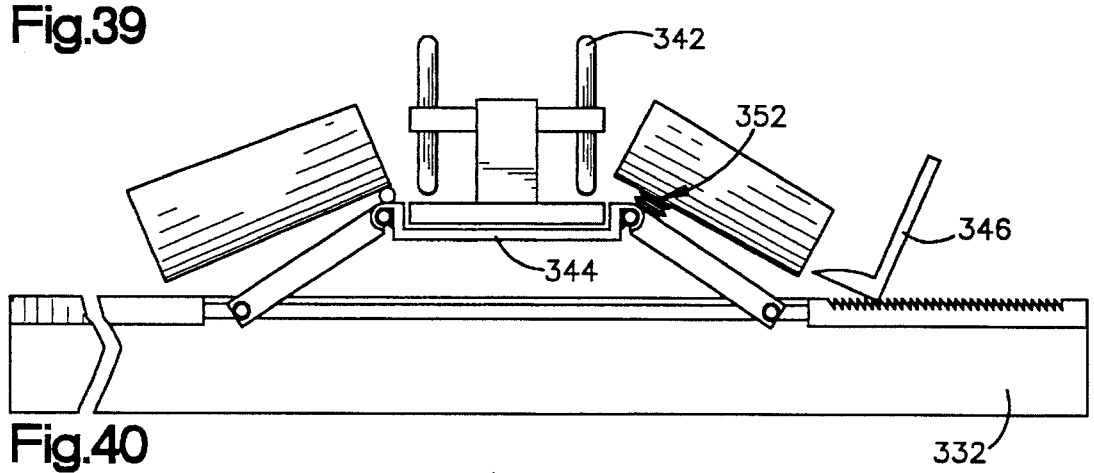
FIG. 40 is a view similar to FIG. 39 with an optional distraction mechanism.

An optional addition to the apparatus 330 is a distraction member 352 (FIG. 40). As illustrated the distraction member 352 is an inflatable bladder having a bellows-type construction for support. The bladder 352 extends between the lower leg panel 354 and the lower leg cuff 334. When the bladder is inflated, it applies force to push the lower leg up to stress the knee outwardly. This can be done to check ligaments in the knee for damage or weakness. This feature of distraction or stressing of a joint can be applied in other joints, on other positioning apparatus, and to move body parts in an manner needed to simulate natural loading of a joint or to enable better imaging of the joint under various conditions.

Thus, it is seen that the present invention provides apparatus for use in imaging which can be attached to an existing table, allows the patient to direct the movement, controls the motion of the joint in a repeatable manner, moves a secondary coil with the joint, and holds the secondary coil in proper alignment. Of course, the movement can be operator controlled, also, by using, for example, a rod attached to the pawl device for moving the patient's foot. Similar constructions as modified can be used to provide for patient directed movement of other body parts and joints.

If a joint is small enough and/or limited enough in its range of motion that imaging the joint with one fixed secondary coil provides acceptable resolution, then it may not be necessary to move the secondary coil. For example, the wrist is a relatively small joint which, even when moved through its entire range of motion, does not take a large amount of space. Thus, the wrist is imaged using flat plates on either side of the wrist or a coil extending around the wrist.

An example of these features is the patient directed apparatus 300 (FIGS. 30–36) for moving the wrist through its range of motion within fixed coils. Similarly, the shoulder is a joint which does not move significantly through space When bent. Accordingly, it can usually be imaged successfully using a fixed coil. In this case, the present invention provides the fixture 200 (FIGS. 24–26) for moving the shoulder through its range of motion within the fixed coil.

However, some joints are large enough and/or move through space so that it is impossible to obtain optimum resolution with a fixed secondary coil through the entire range of motion of the joint. In this case, the present invention provides fixtures for moving the secondary coil with the joint. An example is the movable knee platforms of the table of FIG. 1A. Another example is the apparatus of FIGS. 37–40 for imaging the knee in a patient directed manner with a moving secondary coil.

It should be understood that the present invention contemplates the use of drive or actuating mechanisms other than those shown. For example, any one of the movable portions of the apparatus shown could be driven by a piston-cylinder device which is pneumatic or hydraulic. A pneumatic motor drive could be used, as well as an electric motor drive. Similarly, the pawl and ratchet or detent mechanisms illustrated in FIGS. 30–40 could be used in other configurations, as they are especially suitable for precise, repeatable incremental motion control.

In this regard, reproducability of the movement is desirable so that the patient's progress over a period of time can be checked. Thus, indexing movement of the body part being imaged through degrees or distance is advantageous. Reproducability, as provided by the present invention, is also useful in conducting clinical studies of groups of patients.

In accordance with the present invention, it is possible to use a larger diameter primary coil, allowing increased range of limb movement, without the degradation in image quality which would be expected from the increased coil size. This is possible because of total imaging available with the extensive use of secondary coils as described herein. For example, the knee could be flexed through its entire range of motion to allow optimum imaging of the knee joint. This is currently impossible with the known small primary coils which only allow about 50° of flexion.

Thus, as illustrated in FIG. 41, a known primary MRI coil 360 with a table 362 has a height 361 from the table to the inside of the coil of 16". The table 362 has a width 363 of 19". As illustrated in FIG. 42, a replacement primary MRI coil 364 in accordance with the present invention, with a table 366, has a height 365 from the table to the inside of the coil of 21.5". The table has a width 367 of 24". With these dimensions and the moving secondary coils, substantially increased limb movement is possible, without degradation of image quality.

In a further embodiment of the present invention, an MRI primary coil is mounted to extend vertically rather than horizontally. Thus, as illustrated in FIG. 43, a primary MRI coil 368 extends vertically rather than horizontally. A patient may be placed in a standing or seated position on a support 370 for imaging in the coil 368. A ram 372 is operable to move the patient into and out of the coil. 368. Positioning fixtures, etc. are mounted to a support member 374.

With the patient in a vertical or in a seated position, it is possible to simulate joint positionings and joint loadings which can not readily be simulated when the patient is lying down in a known horizontal imaging coil. For example, a weight or other tractive force can be attached to the arm to simulate shoulder joint loading experienced When carrying a heavy object. The knee can be imaged with the patient standing to see how the joint appears when loaded with body weight. The spine can be imaged when standing or seated to check for disc or vertebral problems which are experienced in normal life but which disappear when the patient lies down to be imaged in a known horizontal imaging coil. The possibilities for increased usefulness of the imaging methodology are manifold.

Any of the positioning apparatus disclosed herein are usable with or without a secondary coil. When used with a secondary coil, they provide the benefit of constraining movement of the secondary coil in a proper planar orientation relative to the primary coil, and also the benefit of keeping the secondary coil in close proximity to the body part being moved and imaged.

If the various apparatus of the present invention are used for magnetic resonance imaging, they must be made of non-ferromagnetic materials plastic is preferred for the table and the positioner, while brass is suitable for mechanical drive mechanisms. Fluid drive mechanisms are also highly suitable because they can be easily constructed using plastic components. Wood is also usable.

From the above description of the invention, those skilled in the art will perceive improvements, changes and modifications in the invention. Such improvements, changes and modifications within the skill of the art are intended to be covered by the appended claims.

I claim:

1. Apparatus for imaging a body part of a patient, said apparatus comprising a primary coil having a chamber for receiving the body part, a secondary coil, means for coupling said secondary coil for movement with the body part, means for moving the coupled body part and secondary coil between a first imaging position and a second imaging position with the body part in the chamber in said primary coil, and means for maintaining said secondary coil in a predetermined orientation relative to said primary coil during movement of the coupled body part and secondary coil between said first and second imaging positions.

2. An apparatus as set forth in claim 1 further including surface means for supporting the patient with the patient lying on his or her back, said means for moving the coupled body part and secondary coil between a first imaging position and a second imaging position including means for raising a portion of said surface means and said secondary coil to hyper-extend the patient's spine while the patient is lying on his or her back on said surface means.

3. An apparatus as set forth in claim 2 wherein said means for raising a portion of said surface means and said secondary coil includes extensible means for holding fluid under pressure and means for conducting fluid to said extensible means to raise the portion of said surface means and said secondary coil.

4. An apparatus as set forth in claim 2 wherein said means for raising a portion of said surface means and said secondary coil includes screw means connected with the portion of said surface means and means for rotating said screw means to raise the portion of said surface means and said secondary coil.

5. An apparatus as set forth in claim 1 further including surface means for supporting the patient with the patient lying on his or her back, said means for coupling said secondary coil for movement with the body part includes means for supporting said secondary coil beneath the back of the patient while the patient is lying on his or her back on said surface means.

6. An apparatus as set forth in claim 5 wherein said means for moving the coupled body part and secondary coil between a first imaging position and a second imaging position includes means for raising a portion of said surface means and said secondary coil to hyper-extend the patient's spine while the patient is lying on his or her back on said surface means and while said secondary coil is beneath the back of the patient.

7. An apparatus as set forth in claim 5 wherein said means for moving the coupled body part and secondary coil between a first imaging position and a second imaging position includes means for lowering a portion of said surface means and said secondary coil to flex the patient's spine while the patient is lying on his or her back on said surface means and while said secondary coil is beneath the back of the patient.

8. An apparatus as set forth in claim 1 further including surface means for supporting the patient with the patient lying on his or her back, said means for moving the coupled body part and secondary coil between a first imaging position and a second imaging position includes means for lowering a portion of said surface means and said secondary coil to flex the patient's spine while the patient is lying on his or her back on said surface means.

9. An apparatus as set forth in claim 8 wherein said means for lowering a portion of said surface means and said secondary coil includes contractible means for holding fluid under pressure and means for conducting fluid from said contractible means to lower the portion of said surface means and said secondary coil.

10. An apparatus is set forth in claim 8 wherein said means for lowering a portion of said surface means and said secondary coil includes screw means connected with the portion of said surface means and means for rotating said screw means to lower the portion of said surface means and said secondary coil.

11. A method of imaging a body part, said method comprising the steps of providing a primary coil having a chamber for receiving the body part, providing a secondary coil, coupling the secondary coil for movement with the body part, moving the body part into the chamber of the primary coil, imaging the body part in a first imaging position with the secondary coil in a predetermined orientation relative to the primary coil, moving the coupled body part and secondary coil to a second imaging position, and imaging the body part in the second imaging position with the secondary coil in the predetermined orientation relative to the primary coil.

12. A method as defined in claim 11 further including the step of maintaining the secondary coil in the predetermined orientation relative to the primary coil during movement of the coupled body part and secondary coil between the first and second imaging positions.

13. A method as defined in claim 11 further including the step of distracting the body part when the body part is in one of the first and second imaging positions.

14. An apparatus for use in imaging a patient, said apparatus comprising a primary imaging coil which extends around an imaging chamber, table means for supporting a patient with at least a portion of said table means and at least a portion of the patient in the imaging chamber, said table means having a movable section which is movable relative to said primary imaging coil to move the portion of the patient in the imaging chamber between a first imaging position and a second imaging position, drive means connected with said movable section of said table means for moving said movable section of said table means and the portion of the patient in the imaging chamber between the first imaging position and the second imaging position, a secondary imaging coil, and means connected with said drive means and said movable section of said table means for supporting said secondary imaging coil in the imaging chamber while the portion of the patient is in the imaging chamber, said drive means being operable to move said secondary imaging coil upon operation of said drive means to move said movable section of said table means.

15. An apparatus for imaging a body part of a patient, said apparatus comprising a primary imaging coil having an imaging area in which the body part is disposed during imaging of the body part, a secondary imaging coil, means for supporting the patient with the patient lying with the body part disposed in the imaging area, said means for supporting the patient includes a base having an upper side surface area which is at least partially disposed beneath the patient when the patient is lying with the body part disposed in the imaging area, a first section connected with and movable relative to said base, and a second section connected with and movable relative to said base, means for moving said first and second sections relative to said base, means connected with said first and second sections for supporting said secondary coil and for maintaining said secondary coil in a predetermined orientation relative to said primary coil during movement of said first and second sections relative to said base, said first and second sections forming a continuation of the upper side surface area of said base when the body part is disposed in the imaging area in a first imaging position, said first and second sections extend upward from the upper side surface area of said base when the body part is disposed in the imaging area in a second imaging position, said secondary coil being disposed at a first level when said first and second sections form a continuation of the upper side surface area of said base, said secondary coil being disposed at a second level which is higher than the first level when said first and second sections extend upward from the upper side surface area of said base.

16. An apparatus as set forth in claim 15 wherein said means for supporting said secondary coil includes surface means for forming a recess in which said secondary coil is disposed.

17. An apparatus as set forth in claim 15 wherein said secondary coil is lower than the upper side surface area of said base when said coupled body part and said secondary coil are in the first imaging position, said secondary coil being at least partially disposed above the upper side surface area of said base when said coupled body part and said secondary coil are in the second imaging position.

18. An apparatus is set forth in claim 15 wherein said means for moving said first and second sections relative to said base includes an inflatable bladder disposed beneath said upper side surface area of said base, said bladder being expandable to move said first and second sections upward relative to said upper side surface area of said base.

19. An apparatus as set forth in claim 15 wherein said means for moving said first and second sections relative to said base includes screw means connected with said first and second sections and means for rotating said screw means.

20. An apparatus as set forth in claim 15 wherein said means for supporting said secondary coil includes means for supporting the secondary coil beneath the body part when said secondary coil is at the first level and when said secondary coil is at the second level.

21. An apparatus as set forth in claim 15 wherein said first and second sections extend downward from the upper side surface area of said base when the body part is disposed in a third imaging position, said secondary coil being disposed at a third level which is lower than the first level when said first and second sections extend downward from the upper side surface area of said base.

22. An apparatus as set forth in claim 21 wherein said means for supporting said secondary coil includes means for supporting the secondary coil beneath the body part when said secondary coil is at the first level, when said secondary coil is at the second level, and when said secondary coil is at the third level.

23. An apparatus as set forth in claim 15 wherein said means connected with said first and second sections for supporting said secondary coil and for maintaining said secondary coil in a predetermined orientation relative to said primary coil during movement of said first and second sections relative to said base includes a movable center section connected with said first and second sections, said center section being at least partially disposed above the upper side surface area of said base with said first and second sections extending downward away from said center section toward the upper side surface area of said base when said secondary coil is disposed at the second level.

24. An apparatus as set forth in claim 23 wherein said drive means is connected with said center section and is operable to raise said center section to move said secondary coil from the first level to the second level.

25. An apparatus as set forth in claim 23 wherein said drive means is connected with said first and second sections and is operable to move said first and second sections relative to each other to move said secondary coil from the first level to the second level.

26. A method of imaging a body part, said method comprising the steps of providing a primary coil having an imaging area in which the body part is disposed during imaging of the body part, supporting the patient with the patient lying on a support structure, providing a secondary coil which is connected with the support structure, imaging the body part with the secondary coil at a first level relative to a base portion of the support structure and with the secondary coil in the imaging area of the primary coil in a predetermined orientation relative to the primary coil, raising the secondary coil from the first level to a second level which is higher than the first level, said step of raising the secondary coil from the first level to the second level includes moving at least a portion of the body part and a portion of the support structure upward relative to the base portion of the support structure along with the secondary coil, and imaging the body part with the secondary coil at the second level relative to the base portion of the support structure and with the secondary coil in the imaging area of the primary coil in the predetermined orientation relative to the primary coil.

27. A method as set forth in claim 26 further including the step of extending the body part while moving the secondary coil between the first and second levels.

28. A method as set forth in claim 26 further including the step of flexing the body part while moving the secondary coil between the first and second levels.

29. A method as set forth in claim 26 wherein said step of imaging the body part with the secondary coil at the first level is performed with the secondary coil beneath the body part, said step of imaging the body part with the secondary coil at the second level is performed with the secondary coil beneath the body part.

30. A method as set forth in claim 26 further including lowering the secondary coil from the first level to a third level which is lower than the first level, said step of lowering the secondary coil from the first level to the third level includes moving at least a portion of the body part and a portion of the support structure downward relative to the base portion of the support structure along with the secondary coil, and imaging the body part with the secondary coil at the third level relative to the base portion of the support structure and with the secondary coil in the imaging area of the primary coil in the predetermined orientation relative to the primary coil.

31. A method as set forth in claim 30 wherein said step of raising the secondary coil from the first level to the second level includes maintaining the secondary coil in the predetermined orientation relative to the primary coil, said step of lowering the secondary coil from the first level to the third level includes maintaining the secondary coil in the predetermined orientation relative to the primary coil.

32. A method as set forth in claim 26 wherein said step of raising the secondary coil from the first level to the second level includes maintaining the secondary coil in the predetermined orientation relative to the primary coil.

33. A method of imaging a body part, said method comprising the steps of providing a primary coil having an imaging area in which the body part is disposed during imaging of the body part, supporting the patient on a support structure, providing a secondary coil which is supported by the support structure, imaging the body part with the secondary coil in the imaging area of the primary coil in a predetermined orientation relative to a base portion of the support structure and with a movable section of the support structure in a first orientation relative to the base portion of the support structure, said step of imaging the body part being performed with the body part in a first orientation relative to the base portion of the support structure, moving the movable section of the support structure from the first orientation to a second orientation relative to the base portion of the support structure, said step of moving the movable section of the support structure from the first orientation to the second orientation includes changing the orientation of the body part from the first orientation to a second orientation relative to the base portion of the support structure, and imaging the body part with the secondary coil in the imaging area of the primary coil and in the predetermined orientation relative to the base portion of the support structure and with the movable section of the support structure in the second orientation of the movable section relative to the base portion of the support structure, said step of imaging the body part with the movable section of the support structure in the second orientation relative to the base portion of the support structure being performed with the body part in the second orientation of the body part relative to the base portion of the support structure.

34. A method as set forth in claim 33 further including the step of maintaining the secondary coil in the predetermined orientation relative to the base portion of the support structure during movement of the movable section of the support structure between the first and second orientations of the movable section and during movement of the body part between the first and second orientations of the body part.

35. A method as set forth in claim 33 wherein said step of moving the movable section of the support structure from the first orientation to the second orientation of the movable section includes moving the secondary coil relative to the base portion of the support structure.

36. A method as set forth in claim 35 further including the step of maintaining the secondary coil in the predetermined orientation relative to the base portion of the support structure during movement of the secondary coil relative to the base portion of the support structure.

37. A method as set forth in claim 33 wherein said step of moving the movable section of the support structure from the first orientation to the second orientation of the movable section of the support structure includes moving the movable section of the support structure relative to the secondary coil.

38. A method as set forth in claim 33 wherein said step of moving the movable section of the support structure from the first orientation to the second orientation of the movable section of the support structure includes conducting fluid to an expandable device and expanding the expandable device under the influence of the fluid conducted to the expandable device.

39. A method as set forth in claim 33 wherein said step of moving the movable section of the support structure from the first orientation to the second orientation of the movable section of the support structure includes rotating a screw member.

40. A method as set forth in claim 33 wherein said step of moving the movable section of the support structure from the first orientation to the second orientation of the movable section of the support structure includes pivoting the movable section of the support structure relative to the base portion of the support structure while maintaining the secondary coil stationary relative to the base section of the support structure.

41. A method as set forth in claim 33 further including the step of connecting the body part with the movable section of the support structure prior to performing said step of moving the movable section of the support structure from the first orientation to the second orientation of the movable section of the support structure.

42. A method of imaging at least a portion of a spine of a patient, said method comprising the steps of supporting the patient with the patient lying on a support surface, providing a secondary coil, positioning at least a portion of the patient and the support surface in an imaging area of a primary coil with the secondary coil in a predetermined orientation relative to the primary coil, thereafter, imaging at least a portion of the patient's spine while the patient is lying on the support surface in the imaging area of the primary coil, while the patient's spine is in a first orientation relative to the support surface, and while the secondary coil is in the predetermined orientation relative to the primary coil, thereafter, changing the orientation of the patient's spine from the first orientation to a second orientation relative to at least a portion of the support surface while the patient is lying on the support surface in the imaging area of the primary coil, moving the secondary coil relative to the primary coil during performance of said step of changing the orientation of the patient's spine from the first orientation to the second orientation, and, thereafter, imaging at least a portion of the patient's spine while the patient is lying on the support surface in the imaging area of the primary coil, while the patient's spine is in the second orientation relative to the support surface, and while the secondary coil is in the predetermined orientation relative to the primary coil.

43. A method as set forth in claim 42 wherein said step of changing the orientation of the patient's spine from the first orientation to the second orientation includes rotating a screw member in the imaging area of the primary coil.

44. A method as set forth in claim 42 wherein said step of changing the orientation of the patient's spine from the first orientation to a second orientation includes flexing at least a portion of the patient's spine while the portion of the patient's spine being flexed is in the imaging area of the primary coil and while the patient is lying on the support surface.

45. A method as set forth in claim 42 wherein said step of changing the orientation of the patient's spine from the first orientation to the second orientation includes hyper-extending at least a portion of the patient's spine while the patient is lying on the support surface.

46. A method as set forth in claim 42 wherein the support surface includes a reference portion and a movable portion which is movable relative to the reference portion of the support surface, said step of changing the orientation of the patient's spine from the first orientation to a second orientation includes moving the movable portion of the support surface relative to the reference portion of the support surface while the movable portion of the support surface is in the imaging area of the primary coil.

47. A method as set forth in claim 42 further including the steps of supporting the secondary coil beneath the spine of the patient during performance of said step of imaging the patient's spine while the patient's spine is in the first orientation relative to the support surface, said step of changing the orientation of the patient's spine from the first orientation to the second orientation includes moving the secondary coil while the secondary coil is in the imaging area of the primary coil and is beneath the patient's spine.

48. A method is set forth in claim 47 wherein said step of changing the orientation of the patient's spine includes moving a portion of the support surface upward while the patient is lying on the support surface in the imaging area of the primary coil, said step of moving the secondary coil includes moving the secondary coil upward.

49. A method as set forth in claim 47 wherein said step of changing the orientation of the patient's spine includes moving a portion of the support surface downward while the patient is lying on the support surface in the imaging area of the primary coil, said step of moving the secondary coil includes moving the secondary coil downward.

50. A method as set forth in claim 42 wherein said step of changing the orientation of the patient's spine from the first orientation to the second orientation includes moving a central portion of the patient's spine upward relative to opposite end portions of the patient's spine.

51. A method as set forth in claim 42 wherein said step of changing the orientation of the patient's spine from the first orientation to the second orientation includes moving a central portion of the patient's spine downward relative to opposite end portions of the patient's spine.

52. A method as set forth in claim 42 wherein said step of moving the secondary coil relative to the primary coil includes maintaining the secondary coil in the predetermined orientation relative to the primary coil as the secondary coil is moved relative to the primary coil.

53. A method of imaging at least a portion of a spine of a patient, said method comprising the steps of supporting the patient with the patient lying on a support structure having a support surface, providing a secondary coil which is supported on the support structure in a predetermined orientation relative to at least a portion of the support structure, moving the secondary coil, at least a portion of the spine of the patient, and at least a portion of the support structure into a chamber of a primary coil with the secondary coil supported on the support structure in the predetermined orientation relative to at least a portion of the support structure, thereafter, imaging at least a portion of the patient's spine while the patient is lying on the support surface with at least a portion of the patient's spine in the chamber of the primary coil, while the patient's spine is in a first orientation relative to the support surface, and while the secondary coil is supported on the support structure in the predetermined orientation relative to at least a portion of the support structure, thereafter, changing the orientation of the patient's spine from the first orientation to a second orientation relative to at least a portion of the support structure while the patient is lying on the support surface with at least a portion of the patient's spine in the chamber of the primary coil, said step of changing the orientation of the patient's spine from the first orientation to the second orientation includes maintaining the secondary coil stationary in the predetermined orientation relative to at least a portion of the support structure, and, thereafter, imaging at least a portion of the patient's spine while the patient is lying on the support surface with at least a portion of the patient's spine in the chamber of the primary coil, while the patient's spine is in the second orientation relative to the support surface, and while the secondary coil is supported on the support structure in the predetermined orientation relative to at least a portion of the support structure.

54. A method as set forth in claim 53 wherein said step of changing the orientation of the patient's spine from the first orientation to the second orientation includes effecting a variation in size of a variable volume chamber by conducting fluid flow along a conduit connected in fluid communication with the variable volume chamber.

55. A method as set forth in claim 53 wherein said step of changing the orientation of the patient's spine from the first orientation to the second orientation includes rotating a screw member in the chamber of the primary coil.

56. A method as set forth in claim 53 wherein said step of changing the orientation of the patient's spine from the first orientation to a second orientation includes flexing at least a portion of the patient's spine while the portion of the patient's spine being flexed is in the chamber of the primary coil and while the patient is lying on the support surface.

57. A method as set forth in claim 53 further including the steps of supporting the secondary coil beneath the spine of the patient in the predetermined orientation relative to at least a portion of the support structure during performance of said step of imaging the patient's spine while the patient's spine is in the first orientation relative to the support surface, said step of changing the orientation of the patient's spine from the first orientation is performed while the secondary coil is in the chamber of the primary coil and is beneath the patient's spine.

58. A method is set forth in claim 53 wherein said step of changing the orientation of the patient's spine includes moving a portion of the support surface and the patient's head upward while the patient is lying on the support surface in the chamber of the primary coil.

59. A method as set forth in claim 53 wherein said step of changing the orientation of the patient's spine includes moving a portion of the support surface and the patient's head downward while the patient is lying on the support surface in the chamber of the primary coil.

60. A method of imaging at least a selected portion of a patient's body, said method comprising the steps of supporting the patient with the patient lying on first and second portions of a support surface, providing a secondary coil, moving at least the selected portion of the patient and at least the first portion of the support surface into an imaging area of a primary coil with the secondary coil in a predetermined orientation relative to the second portion of the support surface, thereafter, imaging the selected portion of the patient while the patient is lying on the support surface, while the selected portion of the patient is in a first orientation relative to the second portion of the support surface, and while the secondary coil is in the predetermined orientation relative to the second portion of the support surface, thereafter, changing the orientation of the selected portion of the patient from the first orientation to a second orientation relative to at least the second portion of the support surface while the patient is lying on the support surface with at least the selected portion of the patient in the imaging area of the primary coil, moving the secondary coil and the first portion of the support surface relative to the second portion of the support surface during performance of said step of changing the orientation of the selected portion of the patient from the first orientation to the second orientation, and, thereafter, imaging the selected portion of the patient while the patient is lying on the support surface with the selected portion of the patient in the imaging area of the primary coil, while the selected portion of the patient is in the second orientation relative to the second portion of the support surface, and while the secondary coil is in the predetermined orientation relative to the second portion of the support surface.

61. A method as set forth in claim 60 wherein said step of changing the orientation of the selected portion of the patient from the first orientation to the second orientation includes effecting a variation in size of a variable volume chamber by conducting fluid flow along a conduit connected in fluid communication with the variable volume chamber.

62. A method as set forth in claim 60 wherein said step of changing the orientation of the selected portion of the patient from the first orientation to the second orientation includes rotating a screw member in the imaging area of the primary coil.

63. A method as set forth in claim 60 wherein said step of changing the orientation of the selected portion of the patient from the first orientation to a second orientation includes flexing a joint in the selected portion of the patient while the joint in the selected portion of the patient is in the imaging area of the primary coil and while the patient is lying on the support surface.

64. A method as set forth in claim 60 wherein said step of changing the orientation of the selected portion of the patient from the first orientation to the second orientation includes hyper-extending a joint in the selected portion of the patient while the joint in the selected portion of the patient is in the imaging area of the primary coil and while the patient is lying on the support surface.

65. A method as set forth in claim 60 further including the steps of supporting a secondary coil beneath the selected portion of the patient during performance of said step of imaging the patient while the selected portion of the patient is in the first orientation relative to the second portion of the support surface, said step of changing the orientation of the selected portion of the patient from the first orientation to the second orientation includes moving the secondary coil while the secondary coil is in the imaging area of the primary coil and is beneath the selected portion of the patient.

66. A method is set forth in claim 65 wherein said step of changing the orientation of the selected portion of the patient includes moving the first portion of the support surface upward while the patient is lying on the support surface, said step of moving the secondary coil includes moving the secondary coil upward.

67. A method as set forth in claim 65 wherein said step of changing the orientation of the selected portion of the patient includes moving the first portion of the support surface downward while the patient is lying on the support surface, said step of moving the secondary coil includes moving the secondary coil downward.

68. A method as set forth in claim 60 further including the steps of supporting the secondary coil beneath a joint in the selected portion of the patient during performance of said step of imaging the selected portion of the patient while the selected portion of the patient is in the first orientation relative to the second portion of the support surface.

69. A method as set forth in claim 60 wherein said step of changing the orientation of the selected portion of the patient from the first orientation to the second orientation includes moving at least part of the selected portion of the patient and the secondary coil upward.

70. A method as set forth in claim 60 wherein said step of changing the orientation of the selected portion of the patient from the first orientation to the second orientation includes moving the selected portion of the patient and the secondary coil downward.

71. A method as set forth in claim 60 wherein said step of moving the secondary coil relative to the primary coil includes maintaining the secondary coil in the predetermined orientation relative to the primary coil.

72. An apparatus for imaging at least a portion of a spine of a patient, said apparatus comprising support means for supporting the patient with the patient lying on his or her back, said support means including a base having an upper side surface area, a first section connected with said base and movable relative to said base between an initial position, a raised position, and a lowered position, a second section connected with and movable relative to said base between an initial position, a raised position, and a lowered position, and a movable center section connected with said first and second sections and movable relative to said base between an initial position, a raised position, and a lowered position, said first section having surface means for engaging an upper portion of the patient's back when said first section is in the initial position, said second section having surface means for engaging a lower portion of the patient's back when said second section is in the initial position, said first, second, and center sections being at least partially disposed above the upper side surface area of said base to hyperextend the patient's spine when said first, second, and center sections are in their raised positions, said first, second, and center sections being at least partially disposed below the upper side surface area of said base to flex the patient's spine when said first, second, and center sections are in their lowered positions, a primary magnetic resonance imaging coil having a chamber for receiving at least a portion of said support means, means for supporting said support means for movement between a first position in which said first, second, and center sections of said support means are disposed outside of the chamber of said primary magnetic resonance imaging coil and a second position in which said first, second, and center sections of said support means are disposed within the chamber of said primary magnetic resonance imaging coil, drive means connected with said support means for moving said first, second, and center sections between their initial, raised and lowered positions while said support means is in the second position to change the orientation of the patient's spine while the patient's spine is in the chamber of said primary magnetic resonance imaging coil, a secondary magnetic resonance imaging coil, and means for supporting said secondary magnetic resonance imaging coil beneath the patient's spine and for moving said secondary magnetic resonance imaging coil with said center section during movement of said center section between its initial, raised and lowered positions.

73. An apparatus as set forth in claim 72 wherein said first and second sections slope downward from said center section toward said upper side surface area of said support means when said center section is in its raised position and said first and second sections are in their raised positions.

74. An apparatus as set forth in claim 72 wherein said drive means includes a bladder which is inflatable to move said first, second, and center sections from their initial positions to their raised positions while said bladder and said first, second, and center sections are disposed within the chamber of said primary magnetic resonance imaging coil, said bladder being deflatable to effect movement of said first, second, and center sections from their initial positions to their lowered positions while said bladder and said first, second, and center sections are disposed within the chamber of said primary magnetic resonance imaging coil.

75. An apparatus as set forth in claim 72 wherein said drive means includes a screw member which is rotatable to effect movement of said first, second, and center sections between their initial, raised and lowered positions.

76. An apparatus as set forth in claim 72 wherein said support means further includes a third section connected with said base and movable relative to said base between an initial position, a raised position and a lowered position, said third section having surface means for engaging a patient's head when said third section is in the initial, raised and lowered positions, said third section being at least partially disposed above the upper side surface area of said base to flex an upper portion of the patient's spine when said third section is in the raised position, said third section being at least partially disposed below the upper side surface area of said base to hyper-extend the upper portion of the patient's spine when said third section is in the lowered position, said apparatus further including second drive means connected with said third section for moving said third section between its initial, raised and lowered positions while said support means is in the second position to change the orientation of the upper portion of the patient's spine while the patient's spine is in the chamber of said primary magnetic resonance imaging coil.

* * * * *